US011861673B2

(12) United States Patent
Bleicher et al.

(10) Patent No.: US 11,861,673 B2
(45) Date of Patent: Jan. 2, 2024

(54) SYSTEM, PLATFORM AND METHOD FOR PERSONALIZED SHOPPING USING AN AUTOMATED SHOPPING ASSISTANT

(71) Applicant: NIKE, Inc., Beaverton, OR (US)

(72) Inventors: David Bleicher, Tel-Aviv (IL); Tamir Lousky, Bat-Yam (IL)

(73) Assignee: NIKE, Inc., Beaverton, OR (US)

( * ) Notice: Subject to any disclaimer, the term of this patent is extended or adjusted under 35 U.S.C. 154(b) by 133 days.

(21) Appl. No.: 16/475,580

(22) PCT Filed: Jan. 3, 2018

(86) PCT No.: PCT/IB2018/050041
§ 371 (c)(1),
(2) Date: Jul. 2, 2019

(87) PCT Pub. No.: WO2018/127811
PCT Pub. Date: Jul. 12, 2018

(65) Prior Publication Data
US 2019/0347703 A1 Nov. 14, 2019

Related U.S. Application Data

(60) Provisional application No. 62/443,275, filed on Jan. 6, 2017.

(51) Int. Cl.
*G06Q 30/00* (2023.01)
*G06Q 30/0601* (2023.01)
*A61B 5/107* (2006.01)

(52) U.S. Cl.
CPC ....... *G06Q 30/0627* (2013.01); *A61B 5/1077* (2013.01); *A61B 5/1079* (2013.01); *G06Q 30/0643* (2013.01)

(58) Field of Classification Search
CPC .............................. G06Q 30/06–08
See application file for complete search history.

(56) References Cited

U.S. PATENT DOCUMENTS

| 4,473,373 A | * | 9/1984 | Weiss | D06F 93/00 8/150 |
| 5,164,793 A | | 11/1992 | Wolfersberger et al. | |

(Continued)

FOREIGN PATENT DOCUMENTS

| CN | 101707946 A | 5/2010 |
| CN | 101819663 A | 9/2010 |

(Continued)

OTHER PUBLICATIONS

A brief history of GPS, Mark Sullivan, 2012 (Year: 2012).*

(Continued)

*Primary Examiner* — Christopher B Seibert
(74) *Attorney, Agent, or Firm* — Banner & Witcoff, Ltd.

(57) ABSTRACT

A system, platform and method for personalized shopping are provided. In some embodiments, a personalized shopping assistant system may include a Point of Sale based automated shopping assistant apparatus, for generating a 3D user shopping profile based on a capture of at least a part of a user's body; a shopping assistant server connected to a shopping assistant database, based in a communications cloud, wherein the user shopping profile is uploaded to the shopping assistant database; a mobile device application for applying the user shopping profile in a store, using the user's mobile device; and multiple product identifiers for enabling the user to capture selected products using the mobile device application, wherein the product identifiers include scannable product data that is stored on the shopping assistant database.

11 Claims, 21 Drawing Sheets

(56) References Cited

U.S. PATENT DOCUMENTS

| | | | |
|---|---|---|---|
| 5,689,446 A | 11/1997 | Sundman et al. | |
| 6,289,107 B1 | 9/2001 | Borchers et al. | |
| 6,546,356 B1 | 4/2003 | Genest | |
| 8,065,200 B2 | 11/2011 | Schwartz | |
| 8,567,081 B2 | 10/2013 | Smith | |
| 8,655,053 B1 | 2/2014 | Hansen | |
| 8,818,883 B2 | 8/2014 | Lawrence et al. | |
| 8,868,157 B1 | 10/2014 | Soliz | |
| 8,908,928 B1 | 12/2014 | Hansen | |
| 9,345,957 B2 | 5/2016 | Geisner et al. | |
| 9,386,889 B2 | 7/2016 | Fischer | |
| 9,449,343 B2 | 9/2016 | Mayerle et al. | |
| 9,462,838 B1* | 10/2016 | Smith | A41H 1/02 |
| 9,477,980 B2 | 10/2016 | Zagel et al. | |
| 9,648,926 B2 | 5/2017 | Marks | |
| 9,799,064 B2 | 10/2017 | Ohnemus et al. | |
| 9,875,546 B1 | 1/2018 | Bhole et al. | |
| 9,996,981 B1 | 6/2018 | Tran et al. | |
| 10,008,040 B2 | 6/2018 | Lam et al. | |
| 10,013,803 B2 | 7/2018 | Mach Shepherd et al. | |
| 10,067,500 B2 | 9/2018 | Hargovan et al. | |
| 10,380,794 B2 | 8/2019 | Hauswiesner et al. | |
| 10,420,397 B2 | 9/2019 | Hei et al. | |
| 10,573,004 B2 | 2/2020 | Husheer | |
| 11,324,285 B2 | 5/2022 | Hei et al. | |
| 11,514,673 B2 | 11/2022 | Lehrich et al. | |
| 2002/0138170 A1 | 9/2002 | Onyshkevych et al. | |
| 2002/0140694 A1 | 10/2002 | Sauer et al. | |
| 2003/0195623 A1 | 10/2003 | Marchitto et al. | |
| 2004/0081336 A1 | 4/2004 | Brooks | |
| 2006/0004592 A1* | 1/2006 | Faith | A47F 10/00 |
| | | | 345/173 |
| 2006/0104503 A1 | 5/2006 | Huang et al. | |
| 2007/0005174 A1 | 1/2007 | Thomas | |
| 2007/0056212 A1 | 3/2007 | Fink | |
| 2008/0040278 A1* | 2/2008 | DeWitt | G06Q 30/0255 |
| | | | 705/44 |
| 2009/0051683 A1 | 2/2009 | Goonetilleke et al. | |
| 2009/0247909 A1 | 10/2009 | Mukumoto | |
| 2009/0287452 A1 | 11/2009 | Stanley et al. | |
| 2010/0111370 A1 | 5/2010 | Black et al. | |
| 2010/0296726 A1 | 11/2010 | Rutschmann et al. | |
| 2011/0047046 A1* | 2/2011 | Torres | G06Q 30/0603 |
| | | | 715/706 |
| 2011/0093344 A1 | 4/2011 | Burke et al. | |
| 2011/0298897 A1 | 12/2011 | Sareen et al. | |
| 2012/0054041 A1 | 3/2012 | Williams | |
| 2012/0085828 A1* | 4/2012 | Ziegler | G09F 3/0335 |
| | | | 235/494 |
| 2012/0106796 A1* | 5/2012 | Jones | G06T 13/40 |
| | | | 345/581 |
| 2012/0249741 A1 | 10/2012 | Maciocci et al. | |
| 2012/0303154 A1* | 11/2012 | Stiernagle | G06Q 30/0601 |
| | | | 705/16 |
| 2013/0080289 A1* | 3/2013 | Roy | G06Q 20/322 |
| | | | 705/26.8 |
| 2013/0095924 A1 | 4/2013 | Geisner et al. | |
| 2013/0100256 A1 | 4/2013 | Kirk et al. | |
| 2013/0114869 A1 | 5/2013 | Hernandez Stark et al. | |
| 2013/0218721 A1* | 8/2013 | Borhan | G06Q 30/0238 |
| | | | 705/26.41 |
| 2013/0246222 A1 | 9/2013 | Weerasinghe | |
| 2013/0307851 A1 | 11/2013 | Hernandez Stark et al. | |
| 2014/0040041 A1 | 2/2014 | Ohnemus et al. | |
| 2014/0089134 A1 | 3/2014 | Linh et al. | |
| 2014/0104395 A1 | 4/2014 | Rohaly et al. | |
| 2014/0108208 A1 | 4/2014 | Piana | |
| 2014/0156449 A1 | 6/2014 | Ganesan et al. | |
| 2014/0176565 A1* | 6/2014 | Adeyoola | G06T 19/006 |
| | | | 345/473 |
| 2014/0180864 A1 | 6/2014 | Orlov et al. | |
| 2014/0244442 A1* | 8/2014 | Hirsch | G06Q 30/0625 |
| | | | 705/26.7 |
| 2014/0270540 A1 | 9/2014 | Spector et al. | |
| 2014/0285646 A1 | 9/2014 | Kahlon | |
| 2014/0320529 A1 | 10/2014 | Roberts et al. | |
| 2014/0337138 A1* | 11/2014 | Chitalia | G06K 19/06028 |
| | | | 705/16 |
| 2014/0358738 A1 | 12/2014 | Ohnemus et al. | |
| 2015/0012380 A1 | 1/2015 | Bank et al. | |
| 2015/0039422 A1 | 2/2015 | Abraham et al. | |
| 2015/0066707 A1 | 3/2015 | Unger et al. | |
| 2015/0066712 A1 | 3/2015 | Altieri | |
| 2015/0127132 A1 | 5/2015 | Nyong'o et al. | |
| 2015/0127363 A1 | 5/2015 | Nyong'o et al. | |
| 2015/0133754 A1 | 5/2015 | Freeman et al. | |
| 2015/0154453 A1* | 6/2015 | Wilf | G06T 7/564 |
| | | | 382/103 |
| 2015/0199816 A1 | 7/2015 | Freeman et al. | |
| 2015/0223730 A1 | 8/2015 | Ferrantelli | |
| 2015/0228084 A1 | 8/2015 | Belyaev et al. | |
| 2015/0258431 A1 | 9/2015 | Stafford et al. | |
| 2015/0328016 A1 | 11/2015 | Summit et al. | |
| 2015/0339752 A1 | 11/2015 | Chetuparambil et al. | |
| 2015/0342266 A1 | 12/2015 | Cooper et al. | |
| 2015/0359461 A1 | 12/2015 | Alfaro et al. | |
| 2016/0063613 A1* | 3/2016 | Zhao | G06Q 30/0643 |
| | | | 705/27.2 |
| 2016/0071143 A1 | 3/2016 | Pokorney et al. | |
| 2016/0081435 A1 | 3/2016 | Marks | |
| 2016/0093085 A1 | 3/2016 | Ray et al. | |
| 2016/0110479 A1 | 4/2016 | Li | |
| 2016/0125499 A1 | 5/2016 | Gooch et al. | |
| 2016/0180391 A1 | 6/2016 | Zabaneh | |
| 2016/0183879 A1 | 6/2016 | Goldish et al. | |
| 2016/0247017 A1 | 8/2016 | Sareen et al. | |
| 2016/0286906 A1 | 10/2016 | Malal et al. | |
| 2016/0350833 A1 | 12/2016 | Andon | |
| 2016/0367191 A1 | 12/2016 | Esposito et al. | |
| 2017/0004568 A1 | 1/2017 | Radner | |
| 2017/0027477 A1 | 2/2017 | Charles et al. | |
| 2017/0056212 A1 | 3/2017 | Jonsson et al. | |
| 2017/0061683 A1 | 3/2017 | Dorin et al. | |
| 2017/0076011 A1 | 3/2017 | Gannon | |
| 2017/0083971 A1 | 3/2017 | Ray et al. | |
| 2017/0169571 A1 | 6/2017 | Hung et al. | |
| 2017/0272728 A1 | 9/2017 | Rafii et al. | |
| 2017/0323299 A1* | 11/2017 | Davis | G06Q 20/204 |
| 2018/0033202 A1 | 2/2018 | Lam et al. | |
| 2018/0035762 A1 | 2/2018 | Towns et al. | |
| 2018/0047200 A1 | 2/2018 | O'Hara et al. | |
| 2018/0160776 A1 | 6/2018 | Hei et al. | |
| 2018/0160777 A1 | 6/2018 | Hei et al. | |
| 2018/0182091 A1 | 6/2018 | MacKinnon et al. | |
| 2018/0218437 A1 | 8/2018 | Rusu et al. | |
| 2018/0240238 A1 | 8/2018 | Husheer | |
| 2018/0247426 A1 | 8/2018 | Gluck et al. | |
| 2018/0300445 A1 | 10/2018 | Schouwenburg et al. | |
| 2018/0300791 A1 | 10/2018 | Ganesan et al. | |
| 2019/0026954 A1 | 1/2019 | Vats | |
| 2019/0028637 A1 | 1/2019 | Kolesov et al. | |
| 2019/0037134 A1 | 1/2019 | Merati | |
| 2019/0082794 A1 | 3/2019 | Liu | |
| 2019/0130788 A1 | 5/2019 | Seaton | |
| 2019/0139252 A1 | 5/2019 | Zaiss et al. | |
| 2019/0188784 A1 | 6/2019 | Bleicher et al. | |
| 2020/0211170 A1 | 7/2020 | Coria Mendoza et al. | |
| 2020/0311429 A1 | 10/2020 | Chen | |
| 2021/0093050 A1 | 4/2021 | Lee et al. | |
| 2022/0183424 A1 | 6/2022 | Nevala et al. | |
| 2022/0202138 A1 | 6/2022 | Hei et al. | |

FOREIGN PATENT DOCUMENTS

| | | |
|---|---|---|
| CN | 201831042 U | 5/2011 |
| CN | 102200437 A | 9/2011 |
| CN | 102466472 A | 5/2012 |
| CN | 102682395 A | 9/2012 |
| CN | 103093543 A | 5/2013 |
| CN | 103597519 A | 2/2014 |
| CN | 104040580 A | 9/2014 |
| CN | 104170519 A | 11/2014 |
| CN | 104699908 A | 6/2015 |

(56) References Cited

FOREIGN PATENT DOCUMENTS

| | | | |
|---|---|---|---|
| CN | 105662681 A | 6/2016 | |
| CN | 106372374 A | 2/2017 | |
| CN | 106942837 A | 7/2017 | |
| JP | H06149376 A | 5/1994 | |
| JP | 2000515088 A | 11/2000 | |
| JP | 2001101272 A | 4/2001 | |
| JP | 2002203167 A | 7/2002 | |
| JP | 2003127994 A | 5/2003 | |
| JP | 2003331108 A | 11/2003 | |
| JP | 2005006905 A | 1/2005 | |
| JP | 2005169015 A | 6/2005 | |
| JP | 2007526028 A | 9/2007 | |
| JP | 2010510587 A | 4/2010 | |
| JP | 2013050937 A | 3/2013 | |
| JP | 2013097799 A | 5/2013 | |
| JP | 2014040231 A | 3/2014 | |
| JP | 2016001360 A | 1/2016 | |
| JP | 2016040649 A | 3/2016 | |
| JP | 2016532197 A | 10/2016 | |
| JP | 201779809 A | 5/2017 | |
| KR | 20100019067 A | 2/2010 | |
| KR | 20100131404 A | 12/2010 | |
| KR | 20120123842 A | 11/2012 | |
| KR | 20120123845 A | 11/2012 | |
| KR | 20130052159 A | 5/2013 | |
| KR | 20140123977 A | 10/2014 | |
| KR | 20150061089 A | 6/2015 | |
| KR | 20150070459 A | 6/2015 | |
| KR | 20160005977 A | 1/2016 | |
| KR | 20160021118 A | 2/2016 | |
| TW | 201251444 A | 12/2012 | |
| WO | 9748027 A1 | 12/1997 | |
| WO | 2005006905 A1 | 1/2005 | |
| WO | 2012072844 A1 | 6/2012 | |
| WO | 2013026798 A1 | 2/2013 | |
| WO | 2014159726 A1 | 10/2014 | |
| WO | 2016051416 A1 | 4/2016 | |
| WO | 2017127132 A1 | 7/2017 | |
| WO | 2017220638 A1 | 12/2017 | |
| WO | 2018048902 A1 | 3/2018 | |
| WO | 2018109421 A1 | 6/2018 | |

OTHER PUBLICATIONS

Heat map definition, Google (Year: NA).*
Xu, Bing, and Yonghai Yu. "A personalized assistant in 3D virtual shopping environment." 2010 Second International Conference on Intelligent Human-Machine Systems and Cybernetics. vol. 2. IEEE, 2010. (Year: 2010).*
Domina, Tanya, Patrick Kinnicutt, and Maureen MacGillivray. "Thermal pattern variations analyzed using 2D/3D mapping techniques among females." Journal of Textile and Apparel, Technology and Management 7.1 (2011). (Year: 2011).*
May 24, 2018—(WO) ISR & WO—App. No. PCT/IB18/050041.
Oct. 1, 2018—(WO) ISR & WO—App. No. PCT/US18/039781.
Jul. 9, 2019—(WO) ISR & WO—App. No. PCT/US19/014958.
Nov. 16, 2017—(WO) ISR & WO—App. No. PCT/US17/050281.
Anonymous: "How to Calculate Height of Android Phone from ground—Stack Overflow". Aug. 17, 2017 (Aug. 17, 2017), XP055836361, Retreived from the Internet: URL:https://stackoverflow.com/questions/17443936/how-to-calculate-height-of-android-phone-from-ground [retreived on Aug. 31, 2021].
Geometrix announces unique web 3D virtual try-on solution. (Oct. 23, 2000). PR Newswire Retrieved from https://dialog.proquest.com/professional/docview/444318359?accountid=161862 (Year: 2000).
"Accu Foot size", Accu foot size app review, Retrieved from the internet <URL https://www.apkmonk.com/app/com.accufootsize/>, 2015, 7 pages.
Mar. 29, 2018 (WO) International Search Report received for PCT Patent Application No. PCT/US2017/065878, 16 pages.
Nov. 19, 2018 (JP) Office Action received for Japanese Patent Application No. 2018-502047, 4 pages (Official Copy only)(See Communication under 37 CFR §v1.98(a)(3)).
Ganesan, Anand, "Footwear Virtual Fitting Service for E-Commerce & Physical Stores", findmeashoe.com, Jul. 2018, 27 pages.
Jun. 27, 2018 (WO) International Preliminary Report on Patentability received for PCT Patent Application No. PCT/US2017/065878, 13 pages.
Schmeil, Andreas, et al., "MARA—A Mobile Augmented Reality-Based Virtual Assistant," Mar. 10, 2007, IEEE Virtual Reality Conference (Year: 2007).
Brykman, Steven, "Get Ready! The Humanoid AR Assistants Are Coming," Oct. 18, 2017, medium.com: Interactive Mind (Year: 2017), 7 pages.
Yang, Yu-I, et al., "A virtual try-on system in augmented reality using RGB-D cameras for footwear personalization," Oct. 2014, Journal of Manufacturing Systems vol. 33, Issue 4 (Year: 2014), 9 pages.
Merriam-Webster Dictionary definitions of "augmented reality," "superimpose," & "real time," as referenced in Response to Arguments, retrieved from merriam-webster.com via Internet Archive, dated 2013-2014 (Year: 2014).
M. Yuan, et al., "A Mixed Reality Virtual Clothes Try-On System," in IEEE Transactions on Multimedia, vol. 15, No. 8, pp. 1958-1968, Dec. 2013, doi: 10.1109/TMM.2013.2280560 (Year: 2013).
Kabir, et al., Review Paper, "Mobile Apps for Foot Measurement: A Scoping Review," arXiv e-prints, Sep. 2020 (Year: 2020), 25 pages.
Dec. 4, 2017 (WO) International Search Report—PCT/US17/43373, 12 pages.
"GPA gait posture assessment", <<https://blog.naver.com/doveman/220777337061>>, Aug. 2, 2016, 14 pages.

* cited by examiner

Isometric View

Front View

Isometric Back

Isometric Front

Top view

Side View

SYSTEM, PLATFORM AND METHOD FOR PERSONALIZED SHOPPING USING AN AUTOMATED SHOPPING ASSISTANT

CROSS-REFERENCE TO RELATED APPLICATIONS

This application is a U.S. National Stage application under 35 U.S.C. § 371 of the International Application PCT/IB2018/050041 (published as WO 2018/127811 A1), filed Jan. 3, 2018, which claims priority from U.S. Provisional Patent Application No. 62/443,275, filed 6 Jan. 2017, entitled "A SYSTEM, PLATFORM AND METHOD FOR PERSONALIZED SHOPPING USING AN AUTOMATED SHOPPING ASSISTANT", the disclosures of which are hereby incorporated by reference in their entirety.

FIELD OF THE INVENTION

The present invention relates in general to methods, applications and devices useful in personalized product shopping.

BACKGROUND OF THE INVENTION

A great majority of shoe shopping today still takes place in real bricks and mortar shops. Most customers are familiar with the limitations of conventional shopping, as are the shop managers and assistants. In general, customers are dependent on shopping assistants, to direct them towards products, location of in-stock products, assistance on trying on products etc.

Further, the typical shopping experience needs to repeated with substantially each visit of a customer to the same or a different shop, leading to great inefficiency and user frustration.

It would be highly advantageous to have a system or method that could enable highly accurate and user friendly automated or semi-automated fitting solutions, both online and instore.

SUMMARY OF THE INVENTION

There is provided, in accordance with an embodiment of the present invention, an apparatus, system, and method to provide personalized online product fitting, according to some embodiments.

A method for personalized shopping has the steps of an automated shopping assistant system accessing product data, a matchmaking system accessing user history data, the matchmaking system accessing user preference data, the matchmaking system accessing user anatomical data acquired from an automated shopping assistant apparatus, the automated shopping assistant system matching user history, preference and anatomical data with product data to generate a personalized matching system.

In some embodiments the automated shopping assistant system matches user history and preference data with product data, to generate personalized product recommendations.

In some embodiments the automated shopping assistant system may be used to enable the user to order personalized products.

In some embodiments the automated shopping assistant system may be used to providing a simulation that represents one or more anatomical characteristics of the user In an embodiment, the user and one or more third parties may provide product fitting feedback, and the user and one or more third parties may provide social feedback. The automated shopping assistant system may adjust the personalized product based on the product feedback. The system may also provide anatomical data about a user, wherein the automated shopping assistant system also considers the anatomical data to generate a user shopping avatar that contains one or more characteristics of the user.

The automated shopping assistant system may include a virtual try-on feature. In an embodiment, before the user orders the personalized product, the product is generated based on the avatar. The user preferences may be selected from the group consisting of size, color, material and type preferences.

According to some embodiments, a platform is provided for personalized shopping, including a cloud based server including a profile module for generating a digital avatar for multiple users, a product module for consolidating product data for multiple products, and a matchmaking module adapted to run code to match the digital avatar data and the product data, to generate product recommendations; an end user computing device, communicatively connected to the cloud based server, including an image capture element, wherein the matchmaking module runs a software application to generate a user mobile shopping avatar based on the capture of at least a part of the user anatomy, to be used in generating anatomical data for the digital avatar profile for a user.

In some embodiments, the platform is adapted to generate and/or present a simulation that represents one or more anatomical characteristics of the user In some embodiments, the platform may have a product ordering module, a product customization module, a social shopping module, and/or a product fitting module etc.

A handheld system for personalized shopping may have a screen configured to receive a user's input, a device camera to capture standard images of a user anatomy, and a processor having registers adapted to analyze anatomical data, product data, user history data and user preference data, wherein the processor retrieves information from the registers, and writes information to the registers, is configured to match user history and preference data with product data to generate a personalized matching system, and the processor is configured to match user history and preference data with product data, to generate a personalized product, and wherein the user may purchase the personalized product by providing user input to the screen.

In one embodiment, the system has a depth sensor configured to accurately determine the distance of a subject from the sensor, and wherein depth sensor information is used to match preference data with product data. In some embodiments, the depth sensor is capable to provide a 3D scan of at least a part of a body that relates to an anatomical profile of a user, to enable capture of length, breadth and depth of the part of the body.

In some embodiments, the handheld system includes a software application running on the handheld system, to generate and present a graphic simulation of a user mobile shopping profile based on the capture of at least a part of the user anatomy.

A shopping assistant system for shopping using a shopping profile is provided, comprising: a POS based automated shopping assistant apparatus, for generating a user shopping profile; a mobile device app for applying the user shopping profile in a store; a shopping assistant server connected to a shopping assistant database, based in a communications cloud; and multiple products recognition devices, such as tags, for enabling the user to capture selected products.

The shopping assistant apparatus may include one or more image scanners for capturing at least a part of a body that relates to an anatomical profile of a user, to enable capture of length, breadth and depth of the part of the body.

The shopping assistant may include a product module for consolidating product data for multiple products; and a matchmaking module adapted to run code to connect the shopping profile and the product data, to generate product recommendations.

The shopping assistant may include an ordering tag associated with a product, for a user to make an order by capturing the ordering tag.

The shopping assistant may include a proximity sensor associated with the shopping assistant apparatus, for identifying a user when the user enters a selected geographical zone around the shopping assistant apparatus.

The shopping assistant may include a proximity sensor associated with the shopping assistant apparatus, for enabling recognition and automatic triggering of a scan when a user is appropriately positioned in the proximity sensor's proximity.

The shopping assistant may include a virtual try-on module, for digitally trying a selected product on a user shopping profile.

A method for in store shopping enhancement is provided, comprising: identifying a user entering a shopping area, using a proximity sensor associated with an automated shopping assistant apparatus; connecting the user to an automated shopping assistant system, to open a user profile; initiate capture of one or more body parts by the automated shopping assistant apparatus, using one or more image sensors; generating a user 3D shopping profile of the user; initiating downloading of an automated shopping assistant Application on the user's mobile computing device; connecting the automated shopping assistant apparatus to the user mobile device, to end the user shopping profile the user mobile device; selecting a product of interest by the user, by capturing a product tab using the user mobile device; and providing the user with product related information for the selected product.

The method may further include ordering a selected product using the user mobile device.

The method may further include customizing a selected product using the user mobile device.

The method may further include ordering a customized product using the user mobile device.

The method may further include providing the user product inventory information

The method may further include generating a user profile avatar. The method may further include fitting the selected product on the user shopping profile avatar.

The method may further include sending the fitted user profile avatar to a social media system for viewing by selected associated connected to the user. The method may further include enhancing the user shopping profile based on the user behaviour.

The method may further include providing shopping recommendations based on the user shopping profile and/or user shopping behavior.

The method may further include using the user shopping profile for shopping in an online store.

The method may further include enhancing the user shopping profile using an additional imaging device.

The method may further include generating additional user shopping profiles using a mobile device.

The method may further include transforming a user's profile data from an in-store device to a user device, such as a smart phone Application, with the users' consent.

A method for personalized shopping is herein provided, comprising the steps of: an automated shopping assistant system accessing product data; the automated shopping assistant system accessing user history data; the automated shopping assistant system accessing user preference data; the automated shopping assistant system accessing anatomical data about a user, wherein the matchmaking system runs a software application to generate a user mobile shopping avatar based on a capture of at least a part of the user anatomy; and the automated shopping assistant system matching user history data, preference data, shopping avatar and product data to generate a personalized matching system.

The method may further include the step of generating a personalized product recommendation.

The method may further include the step of ordering a personalized product.

The method may further include the step of the user and one or more third parties providing product feedback.

The method may further include the step of the user and one or more third parties providing social feedback.

The method may further include the step of the automated shopping assistant system adjusting the personalized product based on the product feedback.

The method may further include the step of providing a simulation that represents one or more anatomical characteristics of the user.

The method may further include a virtual try-on feature.

The method may further include ordering the personalized product, the product is generated based on a user shopping avatar.

The method may further include selecting product types from the group consisting of size, color, material and type preferences.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

The term "fitting" as used herein refers to trying on a product, seeing a product tried on, modifying the product to a particular person's body or other physical parameters. The term "avatar" refers to an embodiment, personification, icon, model or figure representing a particular person, in particular, to represent a person on screen.

The relatively low rate of footwear purchases online shopping may be increased by providing an accurate size recommendation to the customer, optionally based on a simulation or avatar model of a customer's feet, for each shoe model, leading to higher customer confidence in the purchase.

Non-limiting embodiments of the present invention include a system, platform, and method for facilitating highly personalized shopping, whether online and/or in-store, including effective fitting-on of products. In some embodiments, systems, platforms and methods are provided for enabling personalized manufacturing of product.

Figure 1A:
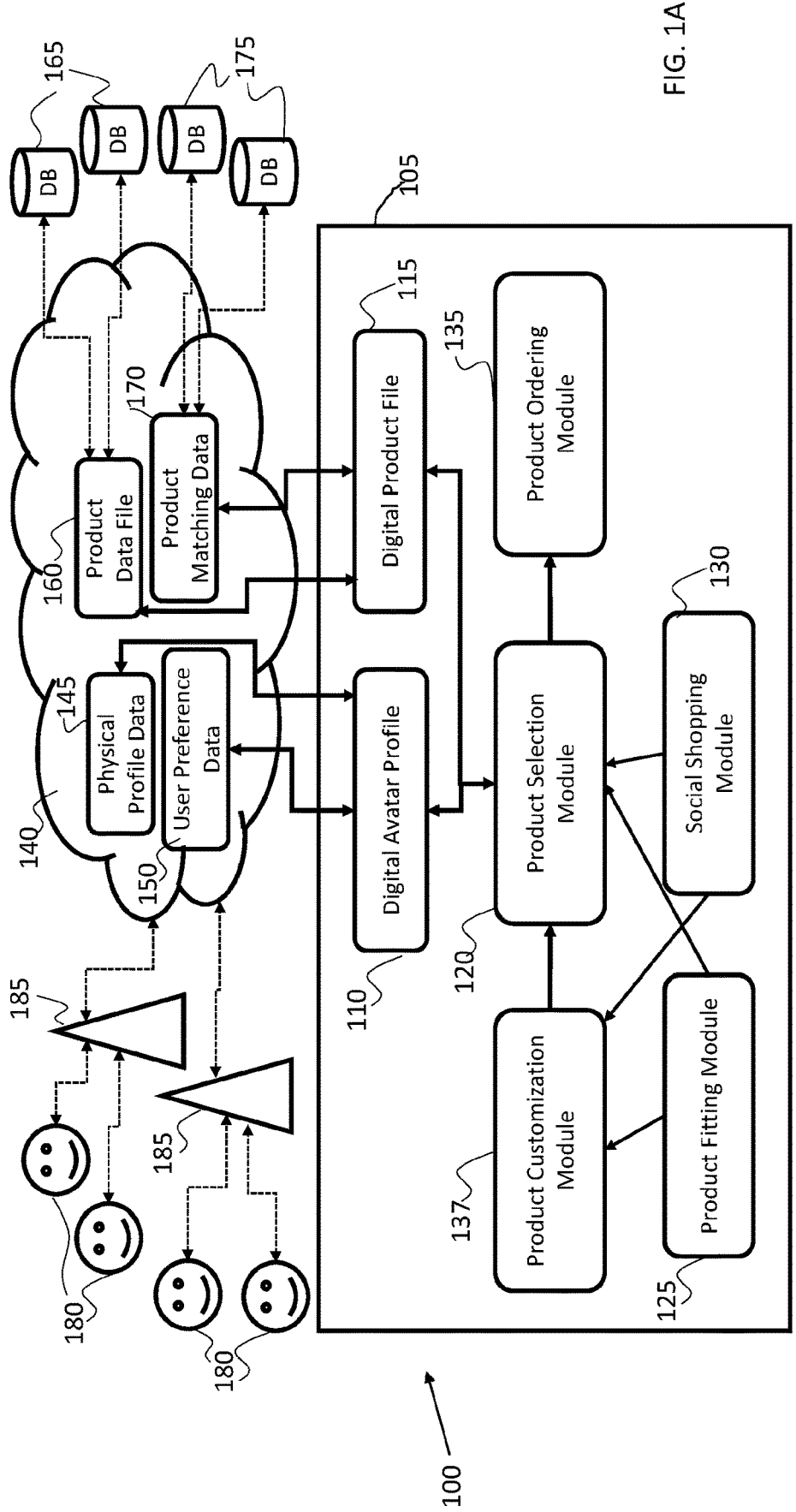
FIG. 1A is a schematic system diagram depicting a system for facilitating personalized shopping, according to some embodiments.

Reference is now made to FIG. 1A, which is a schematic system diagram depicting a system 100 for facilitating personalized shopping, according to some embodiments. System 100 enables seamless shopping in store and/or online, using a highly accurate user shopping profile and/or avatar, generated by an automated shopping assistant apparatus. In some cases data processing is performed on the cloud and/or on the local automated shopping assistant apparatus.

As can be seen, personalized shopping system 100 includes a platform 105 for personalized shopping profile management, which may include a digital avatar profile module 110, a digital product file module 115, a product selection module 120, a product fitting module 125, a social shopping module 130, a product ordering module 135 and a product customization module 137.

Platform 105 is in communication with communications cloud 140, which may include physical profile data module 145, communicatively connected to launch pad, kiosk, or automated shopping assistant apparatus 185, which is further connected communicatively to users 180, providing physical user data, for example, from 2D and/or 3D scans or other digital measurement sources. Communications cloud 140 may further include user preference data module 150, communicatively connected to automated shopping assistant apparatus 185, and/or to 180, providing user preference data. Communications cloud 140 may further include product file data module 160, communicatively connected to product databases 165, and product matching data module 170 containing product matching algorithms, communicatively connected to product databases 175.

In one embodiment, apparatus 185 includes one or more imaging devices, such as 2D and/or 3D cameras, that may be moving or static components. Apparatus 185 may further include one or more sensors, for example, a proximity sensor, scanner, camera, pressure plate and/or other sensors.

As can be seen, digital avatar profile 110 is highly personalized, constructed from various data sources, whether directly or indirectly from a user, and whether representing physical characteristics and/or mental, emotional, psychological characteristics. Digital avatar profile 120 generally includes a file or group of files and data points from which instructions can be executed to enable the generation of a high resolution user profile or avatar from one or more data sources. Further, product selection module 120 generally matches up personalized avatar profile 110 with selected digital products, whether online or offline. The calculations for the matching algorithm may be performed by a processor through storage, retrieval and processing of data. In some embodiments one or more device registers may be used, wherein the register(s) refers to one of a small set of data holding places that are part of a computer processor, for holding a computer instruction, a storage address, or any kind of data. The matching algorithm, in some embodiments, may include running code to provide perfect or close to perfect matches between product types, sizes, styles etc. provided by a product database, and the physical parameters and/or user preference data as defined by the user Avatar profile, based at least on a scan of at least a part of the user's body that relates to the user's profile. For example, user A may have a foot profile that is defined by a size, width, and depth. Further the user's profile may include preference data such as preferred styles, shoe types and colors, such as a blue or grey athletic shoe. The Product database may include, for example, an athletic shoe is colors blue, grey and blue-grey, in the precise or close enough to the user's size, width and depth. In this case, the matching algorithm will match the profile definitions with the one or more products from the product database that match the user profile.

Product selection module 120 may be further refined by providing system feedback and product fitting data using product fitting module 125, as well as social shopping data from social shopping module 130. Product fitting module, in some embodiments, includes a means for feedback from a shopping assistant or supporter that is with the shopper. In other embodiments, product fitting module includes a means for feedback from a virtual shopping assistant or supporter, for example, a communicatively connected supporter, a digital or virtual mirror or screen showing the user with the product. Further, product customization module 137 may receive data from product fitting module 125 and/or social shopping module 130, to help further personalize the product being considered for acquisition in accordance with the digital avatar and the product fitting module 125 and/or social shopping module 130. Product customization module 137 may enable a user to change or customize the product being tried on or tested, for example, by changing product colors, shape, design, size, materials etc. In this way, the product to be ordered may be constructed in accordance with user specific or customized requirements. Further, the Product customization module 137 may send to the product selection module 120 the customized product as chosen or generated by the user, after which the product selection module 120 may initiate the ordering of the customized product, via the product ordering module 135. Moreover, user updates embodied in the user's changes made in product selection module 120 may be used to update the digital avatar profile 110, thereby keeping the user avatar profile updated, for example, to user body changes, preference changes, etc.

Product selection module 120 includes a file or group of files and data points from which instructions can be executed to execute commands to enable the matching of high resolution user profiles or avatars to products that have a high level of fit to the shopping research being performed by each system user. This module may further integrate the feedback generated in the system modules to constantly improve the accurate product recommendation it provides. Using a variety of technical procedures that are performed on the avatar, such as integrating volume, cross section area and circumferences as well as length, width, height and additional distances, the system may represent the avatar in an array of representing numbers. This array of numbers, in some embodiments, may represent the various elements of the avatar, to allow for comparison to similar elements of the products to be tried on by the avatar. Accordingly, when the avatar data, which may be enhanced using recommendation algorithms and machine learning techniques etc, is compared to the product data from the product file, this may allow for an accurate, constantly improving, personalized product recommendation from the system.

According to some embodiment, digital avatar profile can be generated with relatively Low level integration of 3D scanners. In some examples sensors or scanners that may be used may include structured light, time-of-light, photogrammetry, or any other type of 3D and/or 2D scanning technology. Suppliers of such technology, include, but not limited to, are PrimeSense™ based scanners, Occipital Structure Sensors, 3D-Systems Sense and iSense™ sensors, Intel™ RealSense sensors (stand alone or machine integrated), Scanning Platforms based on iPad s or tablets, PC (Integrated and External), Android+RealSense (Next generation) devices, and Google project Tango devices etc.

Figure 1B:
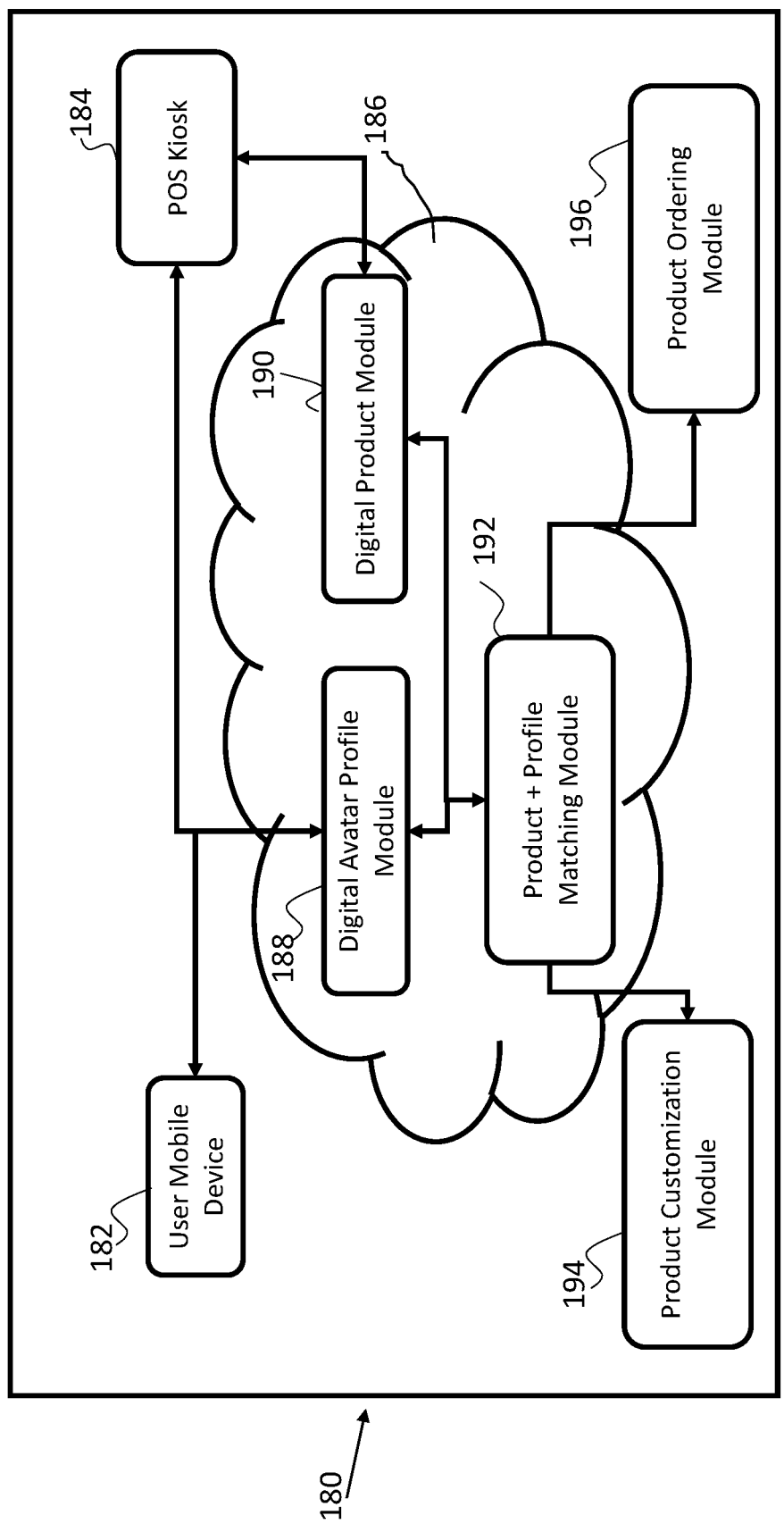
FIG. 1B is a schematic system diagram depicting a platform for facilitating personalized shopping, according to some embodiments.

Reference is now made to FIG. 1B, which is a schematic system diagram depicting a platform 180 for facilitating personalized shopping, according to some embodiments. As can be seen, personalized shopping platform 180 includes one or more user mobile devices 182, such as smartphones or tablets, including, without limitation, a camera, application and data connectivity; a shop or point of sale computing device, kiosk or automated shopping assistant apparatus 184, typically at or near a shop, for example an electronic device with a one or more cameras, sensors or scanning devices, Application, and data connectivity; where mobile device(s) 182 and or automated shopping assistant apparatus 185 connect to the communications cloud 186. Communications cloud 186 includes a digital product module 190, for holding, consolidating and otherwise managing data for multiple products; a digital Avatar profile module 188, for holding, consolidating, processing and otherwise managing profile data for multiple users; and matching module 192, for matching product and avatar profile data, to assist in enabling product recommendations and other matching functions. Platform 180 further includes a product customization module 194, for enabling ordering of customized products based on matching module output and or user choices; and Product ordering module 196, for enabling ordering of products based on the based on matching module output and or user choices.

Figure 2:
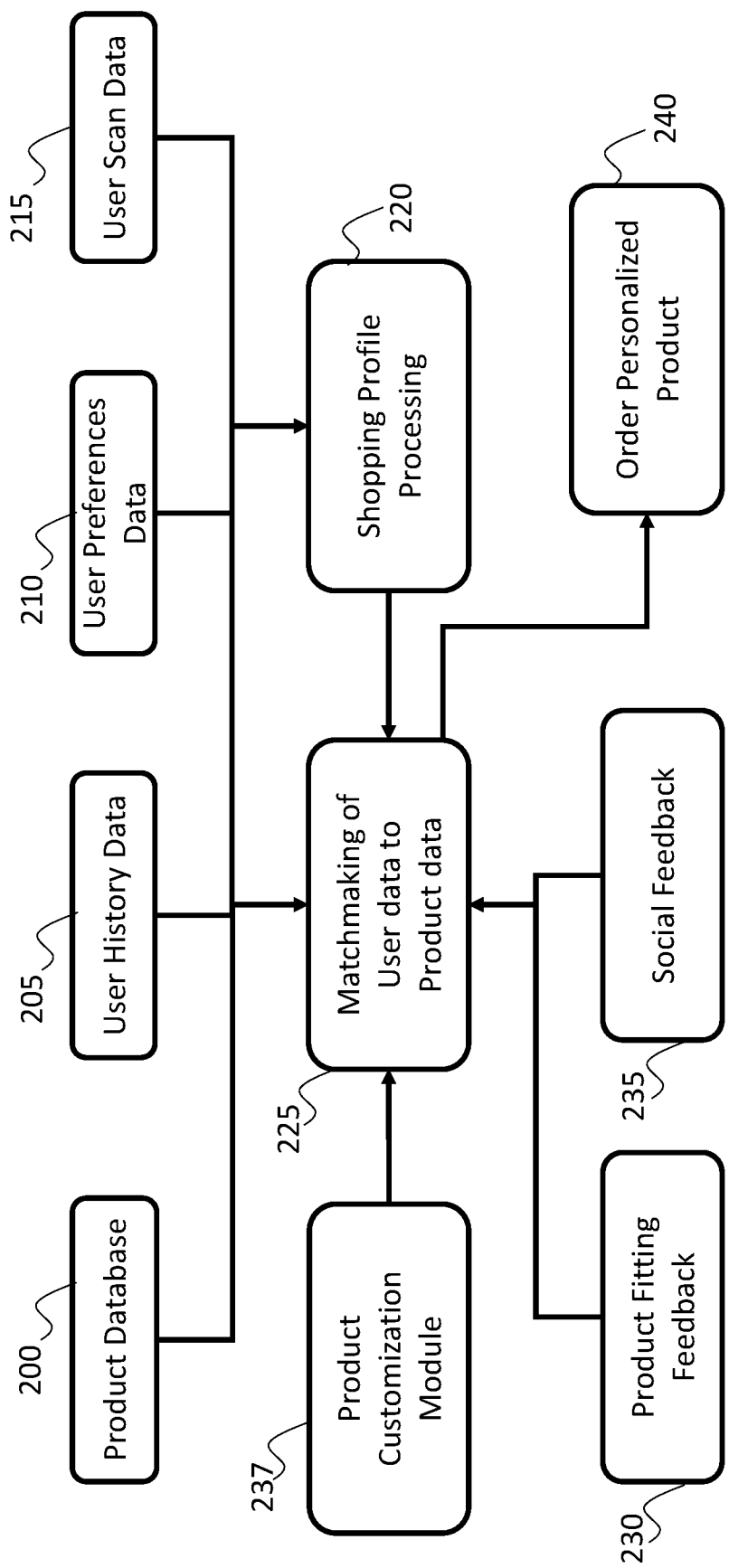
FIG. 2 is a flow diagram indicating a process of facilitating personalized shopping, according to some embodiments.

Reference is now made to FIG. 2, which is a is a flow diagram indicating a process of facilitating personalized shopping, whether online or offline, according to some embodiments. As can be seen, product information from a product database 200 may be used for products to be discovered, purchased or manufactured. At step 205 history data for a user may be retrieved, for example, based upon previous user purchases and research. At step 210 user preference data may be acquired, such as size, color, material, type preferences etc. At step 215, scanned or graphic data may be acquired for a user, for example, from standard photographs, 2D and/or 3D image scanning, or from capture and processing using a POS Kiosk or automated shopping assistant apparatus etc. This graphic data is used by the personalized shopping system to generate a user's physical profile based on the user's physical properties. At step 220 a multi-dimensional user shopping profile, hereinafter referred to as a user shopping avatar, may be developed, by processing the various input data from steps 205, 210 and 215, thereby generating a user shopping avatar or profile that includes user physical properties as well as user behavior and user preference data. The profile or avatar is a dynamic structure which may constantly improve in the way it animates, reflects or represents the user, optionally using feedback and additional inputs from steps 205, 210, and/or 215. In one implementation, a user avatar may be used to match a user to potential products, in a single store, and/or in multiple stores, for example, in any retail store in a chain of stores, or online, in a network or affiliation of online and/or offline stores or platforms.

At step 225, a matchmaking of the user shopping profile to products being researched or required is executed. At this step, the product data from product database 200 is matched to products being researched by a user, in accordance to the specific user shopping profile, thereby enabling advanced filtering out of non-appropriate products for the specific user, and the advanced matching up of appropriate products, in accordance with the specific user's personal shopping profile and preferences. The step of matching may be complemented by a provision of recommendations for the user, based on the above user profile to product matchmaking process. In some embodiments, the generating of a match between a generated user profile and multiple products that fit one or more elements of the generated profile is provided, thereby enabling, for example, fit and size recommendations as well as additional data connecting the profile and the product(s).

At step 230 product fitting data from feedback of physically present personnel or remote people may be used to help modify the matchmaking of user data to product data, for example, the feedback from a salesperson in a store may be used to update the user profile, or the feedback from remote people connected via a smart phone or computer for example. In some cases, for example, salesperson or friend feedback, such as which colors look good on a person or which size looks best etc. may be used by the user to update their shopping profile. In some cases, advanced graphic processing and 3D rendering may be used for the user to virtually try on the product being researched, such that the users may see themselves dressed in the product in accordance with a digital simulation that places the product onto the user shopping avatar. In some cases, the system may provide a static or dynamic high resolution visual output such as an animated avatar or character, rendered pictures and/or visual representation of the recommendation, optionally fitted on the avatar. For example, such a rendition may allow the user to see the product being tried on to be depicted on the avatar, thereby helping the user to visualize details such as fit, tightness, color, style, material etc., according to color heat maps etc. For example, color heat maps may be used to indicate areas of tightness, tension, friction etc. when the product interfaces with the body. As above, the user may use the shopping Avatar to provider further feedback to modify the user's shopping profile. At step 235 feedback may be acquired from social networks or direct third party feedback to which a user is connected, to help modify the user shopping profile.

At step 237, product customization may integrate data from product fitting feedback at step 230 and/or social feedback at step 235, to help further personalize the product being considered for acquisition in accordance with the digital avatar and the product fitting module 125 and/or social shopping module 130.

At step 240, a personalized product may be ordered by a user, whether inside a physical store or an online store. Further, a personalized product may be ordered from a manufacturer who may produce a product based upon the user's request such that the product is a once-off customized product for a user. The custom products may include, for example, various types of customization including material type, print samples, color, size, volume, angles, model variation, styles. Personal tailoring etc.

Figure 3:
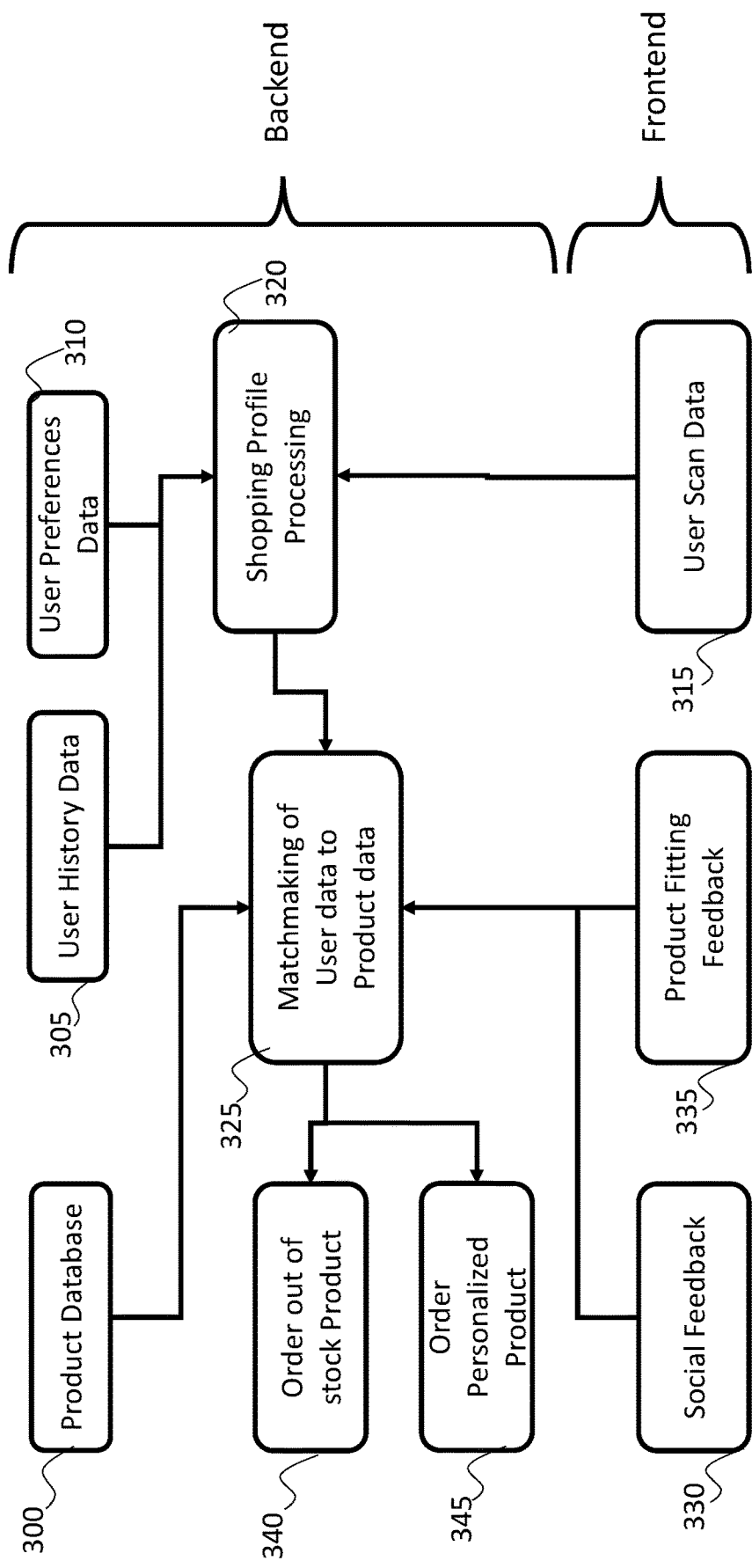
FIG. 3 is a flow diagram for facilitating a personalized in-store shopping experience, according to some embodiments.

Reference is now made to FIG. 3, which is a flow diagram for facilitating a personalized offline (in the store) shopping experience, according to some embodiments. As can be seen, at the backend or computing system supporting a physical store, product information from a product database 300 may be used for products to be discovered, purchased or manufactured by an online user. In some embodiments product database is associated with a product data processing module, which is adapted to perform high intensity calculations on the local point-of-sale device and/or on the cloud, depending on the embodiment type and requirements. At step 305 history data for a user may be retrieved, for example, based upon previous user purchases in a store or chain of stores. At step 310 user preference data may be acquired, such as size, color, material, type preferences etc. At step 315, at the frontend or user side, scanned or graphic data may be acquired for a user, for example, from standard photographs, 2D and/or 3D image scanning, or from capture and processing using a POS Kiosk or apparatus etc. In some embodiments a dedicated or generic application on a smart phone, tablet or other computing device may be used to enable effective photographing or scanning of a user. In further embodiments a dedicated or generic camera or scanning device, kiosk or standing station (moving or static) may be used by a shopping assistant, helper, sales person and/or associate. At step 320, this geometrical data is used by the personalized shopping system, together with the various input data from steps 305 and 310, to generate a multidimensional user shopping avatar or profile that includes user physical properties as well as user behavior and user preference data. In some cases, the profile may be activated, for example of an end user device, web server etc.

At step 325, a matchmaking of the user shopping profile to products being researched or required is executed. At this step, the product data from product database 300 is matched to products being requested by a user, in accordance to the specific user shopping profile. The step of matching may be complemented by a provision of recommendations for the user, based on the above user profile to product matchmaking process, thereby enabling advanced filtering out of non appropriate products for the specific user, and the advanced matching up of appropriate products, in accordance with the specific user's personal shopping profile and preferences. This advanced filtering enables a shop salesperson, for example, or the user themselves, to be presented with substantially appropriate products, optionally products that are currently available, rather than have the user select items that are non appropriate, thereby wasting time and resources of shopping assistants and the shopper themselves. This also allows for users to benefit from matching and recommendation data, which was generated for other avatars or users, which may share similar features, optionally in an anonymized manner, thus enabling a smarter and more accurate matching and/or recommendations.

At step 330 product fitting data from feedback of physically present personnel or remote people may be used to help modify the matchmaking of user data to product data, for example, the feedback from a salesperson in a store may be used to update the user profile, or the feedback from remote people connected via a smart phone or computer for example. In some cases, for example, salesperson or friend feedback, such as which colors look good on a person or which size looks best etc. may be used by the user to update their shopping profile. At step 335 feedback may be acquired from the users, using an active and/or passive approach. For example, active entry of feedback may occur when the system receives actual feedback about the fit (e.g., good/bad/off by how much) or other aspects, whether from a present person or people and/or a remote person or people. Such feedback may allow a user to, for example, enter selected choices into the system, for example, via a box or text entry element where the user may enter a selected size, type or other preference. Passive feedback may occur when the system receives actual feedback about the fit or other aspects, originating from sales information, returns, etc., or by trying on certain types, colors, sizes etc., enables the system to learn from the user's past choices and behavior, to further improve the personal avatar as well as the product information and fit for other users. In some cases, advanced graphic processing and 3D rendering may be used for the user to try on the product being researched, such that the user may see themselves virtually dressed in the product in accordance with a digital simulation that places the product onto the user shopping avatar. As above, the user may use the shopping Avatar to provider further feedback to modify the user's shopping profile.

At step 340, a personalized product may be ordered by a user from a physical store, for example, for a product that is in principle available but not currently in the store, or to enable manufacturing of a specifically required product based upon the user's shopping avatar, such that the product is a once-off customized product for a user.

At step 345 the user can select a personalized product and/or modify or design a product, optionally based on a product which s/he has seen, liked and chosen in the store, to purchase a custom product which will be created and/or manufactured for her/him. These modifications may include visual changes, such as name engraving, colors, materials, prints etc., as well as physical properties, such as controlling the height of the heels in shoes, the thickness of a frame in eyewear etc. At steps 340 and 345, these features may allow the in-store customers to enjoy features that are typically limited to eCommerce and online shopping.

Figure 4:
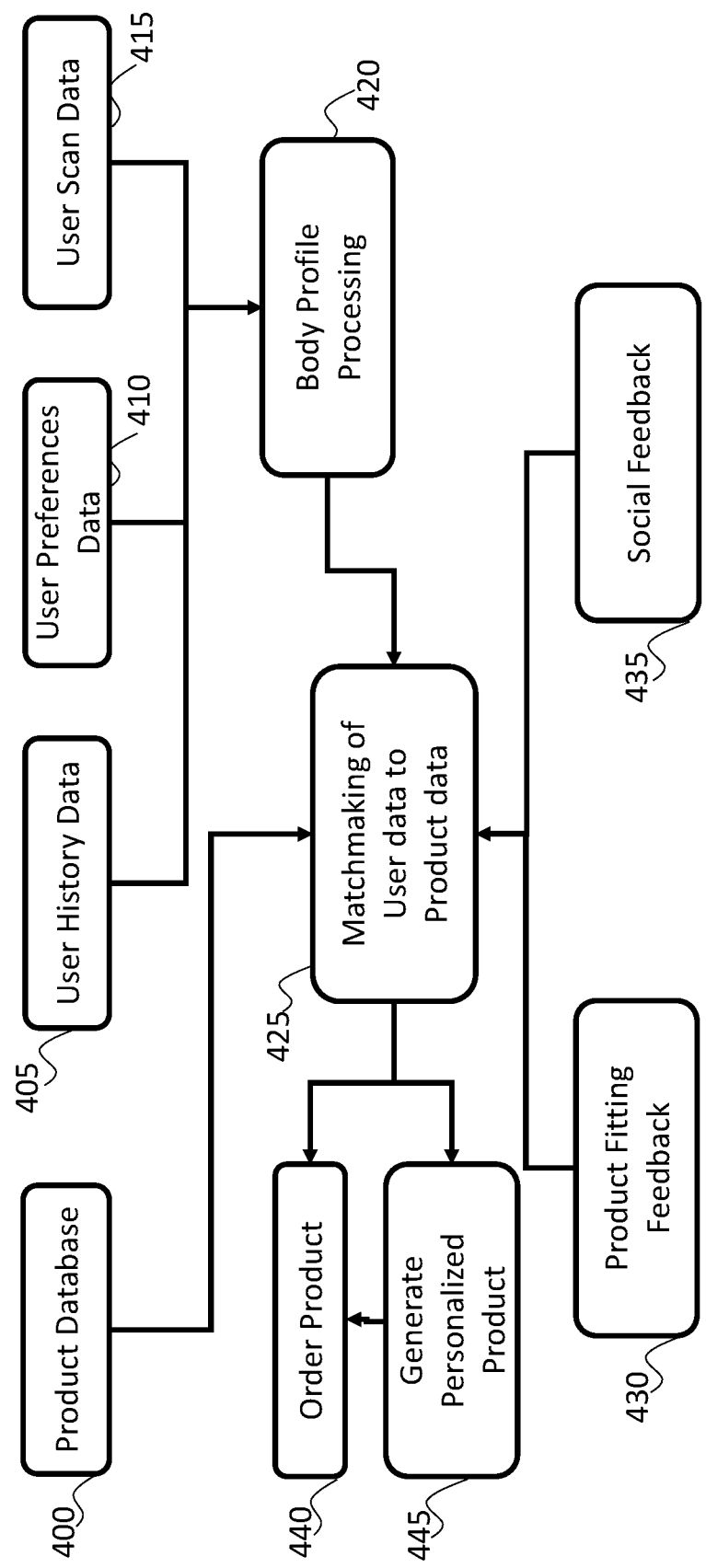
FIG. 4 is a flow diagram for facilitating a personalized online shopping experience, according to some embodiments.

Reference is now made to FIG. 4, which is a flow diagram for facilitating a personalized online shopping experience, according to some embodiments. As can be seen, an online store may acquire product information from a product database 400, for a selection of products to be offered to online users. At step 405 history data for an online user may be retrieved, for example, based upon previous user purchases and research. At step 410 user preference data may be acquired, such as size, color, material, type preferences etc. At step 415, scanned or graphic data may be acquired for a user, for example, from standard photographs, 2D and/or 3D image scanning, or from capture and processing using a POS Kiosk or apparatus etc. In some embodiments a dedicated or generic application on a smart phone, tablet or other computing device may be used to enable effective photographing or scanning of a user. In other embodiments a webcam, 3D camera, video recorder etc. may be used to acquire scanned or graphic data. At step 420, this graphic data is used by the personalized shopping system, together with the various input data from steps 405, 410 and 415, to generate a multidimensional user shopping avatar or profile that includes user physical properties as well as user behavior and user preference data.

At step 425, a matchmaking of the user shopping profile to products being researched or required is executed. At this step, the product data from product database 400 is matched to products being researched by a user, in accordance to the specific user shopping profile, thereby enabling advanced recommending of product matches, for example, to aid filtering out of non appropriate products for the specific user, and the advanced matching up of appropriate products, in accordance with the specific user's personal shopping profile and preferences.

At step 430 product fitting data from feedback of remote people, such as family members, friends or shopping assistants connected via a smart phone or computer for example, may be used to help modify the matchmaking of user data to product data, for example, to include data relating to which colors look good on a person or which size looks best etc. may be used by the user to update their shopping profile. In further examples, code may be used to provide product color recommendations, size or fit recommendations etc. This feedback may be collected actively from the user or statically, for example based on the purchase information, shipping and return shipping data etc. At step 435 feedback may be acquired from social networks or to which a user is connected, to help modify the user shopping profile. In addition, a human and/or machine based digital representative, style expert and/or additional guiding information may be inputted to improve the guidance and support provided to the shopper in the online purchase process. In some cases, advanced graphic processing and 3D rendering may be used to enable the user to virtually try on the product being researched, such that the user may see themselves dressed in the product in accordance with a digital simulation that places the product onto the user shopping avatar. This may be done using real-time simulation, allowing for a live stream of animated video or high resolution images of the simulation etc. The "digital try-on", in some embodiments, may include a physics simulation to include the exact positioning of the element on the avatar in movement on in a static position. As above, the user may use the shopping Avatar to provider further feedback to modify the user's shopping profile.

At step 440, a product may be ordered by a user from an online store. Optionally, at step 445, a personalized product may be generated by a user from an online store, to enable manufacturing of a specifically required product based upon the user's shopping avatar, such that the product is a one-off customized product for a user. The shopping system, in case of a custom manufacturing output, may if needed, connect directly to the company production hardware and ERP system to facilitate such personalized product manufacturing. in one example, the personalized product may be represented in 3D printer files such as STL models or digital cutting devices, such as DXF or DWG files. In other embodiments, this could be a custom routing card or production instruction and BOM files. Additional input may include be visual renders that will help a product manufacturer or printer to visually design the custom product.

In some embodiments, the data from product database 400 may be used, together with the body or avatar profile derived in step 420, to develop a customized product at step 445, optionally without product matchmaking at step 425.

Figure 5:
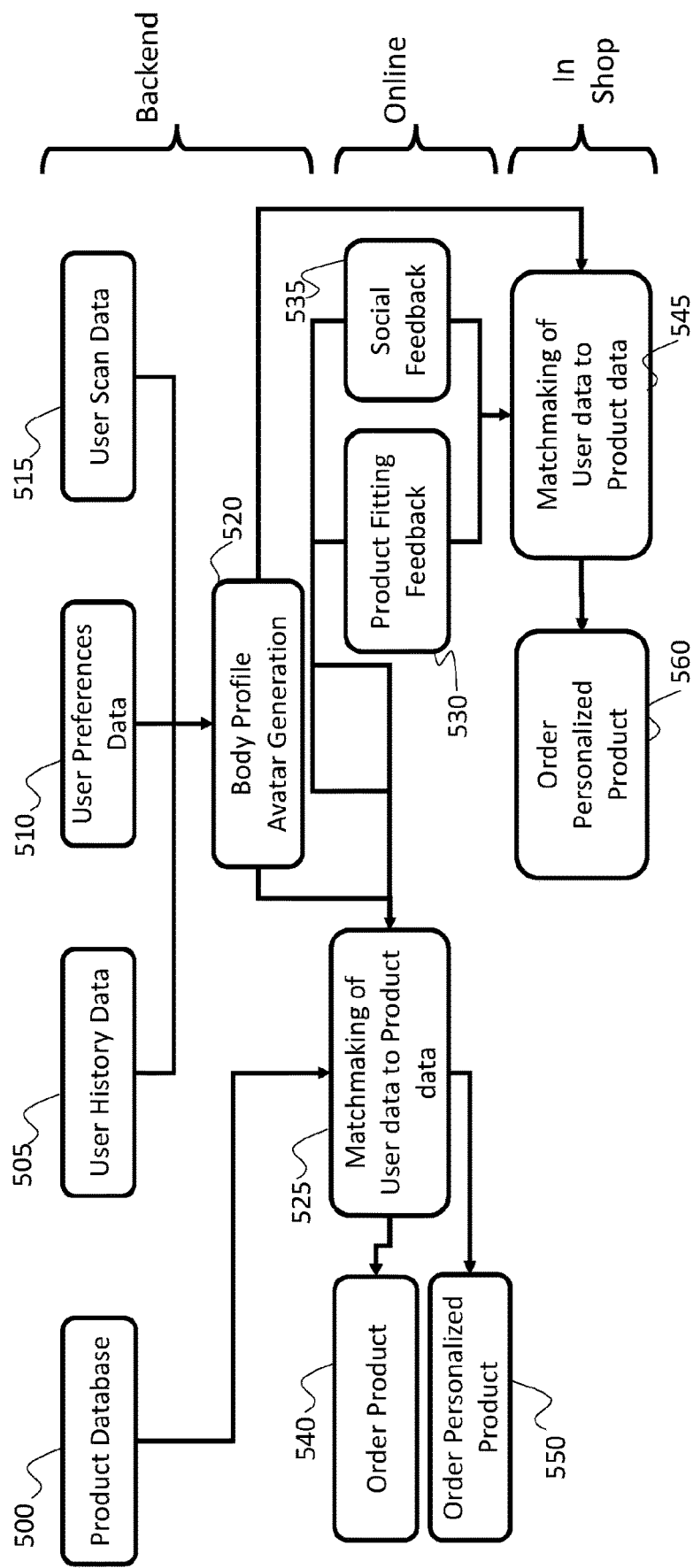
FIG. 5 is a flow diagram indicating an example of personalized hybrid shopping experience, according to some embodiments.

Reference is now made to FIG. 5, which is a flow diagram indicating an example of personalized hybrid shopping experience, according to some embodiments. As can be seen in the figure, at the backend or computing system supporting a physical and/or online store, product information from a product database 500 may be used for products to be discovered, purchased or manufactured by an online or in store user. At step 505 history data for a user may be retrieved, for example, based upon previous user purchases in a store or chain of stores, whether from online and/or in store experiences. At step 510 user preference data may be acquired, such as size, color, material, type preferences etc. At step 515, at the frontend or user side, whether executed by the user or by a shopping assistant, scanned or graphic data may be acquired for a user, for example, from standard photographs, 2D and/or 3D scanning, or from capture and processing using a POS Kiosk etc. In some embodiments a dedicated or generic application on a smart phone, tablet or other computing device may be used to enable effective photographing or scanning of a user. In further embodiments a dedicated or generic camera or scanning device may be used by a shopping assistant, which may include portable or non-portable devices, kiosk type or stand-alone devices. At step 520, this graphic data is used by the personalized shopping system, together with the various input data from steps 505, 510 and 515, to generate a multidimensional user shopping avatar or profile that includes user physical properties as well as user behavior and user preference data. One advantage of this system is the seamless transfer in which the users can transition between online and offline shopping, while enjoying the benefits of personalization, using a constantly updated personal profile in the online and/or in-store scenarios.

In some embodiments, at step 525, a matchmaking of the user shopping profile to products being researched or required is executed, for an online shopping optionally located in a physical store. At this step, the product data from product database 500 is matched to products being requested by a user, in accordance to the specific user shopping profile, thereby enabling advanced filtering out of non appropriate products for the specific user, and the advanced matching up of appropriate products, in accordance with the specific user's personal shopping profile and preferences. This advanced filtering enables a shop salesperson, for example, or the user themselves, to be presented with substantially appropriate products, optionally products that are currently available, rather than have the user select items that are non appropriate, thereby wasting time and resources of shopping assistants and/or the shopper themselves.

At step 530 product fitting data from feedback of physically present personnel or remote people may be used to help modify the matchmaking of user data to product data, for example, the feedback from a salesperson in a store may be used to update the user profile, or the feedback from remote people connected via a smart phone or computer for example. In some cases, for example, salesperson or friend feedback, such as which colors look good on a person or which size looks best etc. may be used by the user to update their shopping profile. At step 535 feedback may be acquired from social networks or to which a user is connected, to help modify the user shopping profile. In some cases, advanced graphic processing and 3D rendering may be used for the user to virtually try on the product being researched, such that the user may see themselves dressed in the product in accordance with a digital simulation that places the product onto the user shopping avatar. As above, the user may use the shopping Avatar to provider further feedback to modify the user's shopping profile.

At step 540, a product may be ordered by an online user in a physical store. At step 550, a personalized product may be ordered by an online user in a physical store, for example, for a product that is in principle available but not currently in the store, or to enable manufacturing of a specifically required product based upon the user's shopping avatar, such that the product is a once-off customized product for a user.

In some embodiments, at step 545, a matchmaking of the user shopping profile to products being researched or required is executed, for user located in a physical store. At this step, the product data from product database 500 is matched to products being requested by a user, in accordance to the specific user shopping profile, thereby enabling advanced filtering out of non appropriate products for the specific user, and the advanced matching up of appropriate products, in accordance with the specific user's personal shopping profile and preferences. This advanced filtering enables a shop salesperson, for example, or the user themselves, to be presented with substantially appropriate products, optionally products that are currently available, rather than have the user select items that are non appropriate, thereby wasting time and resources of shopping assistants and/or the shopper themselves.

Figure 6:
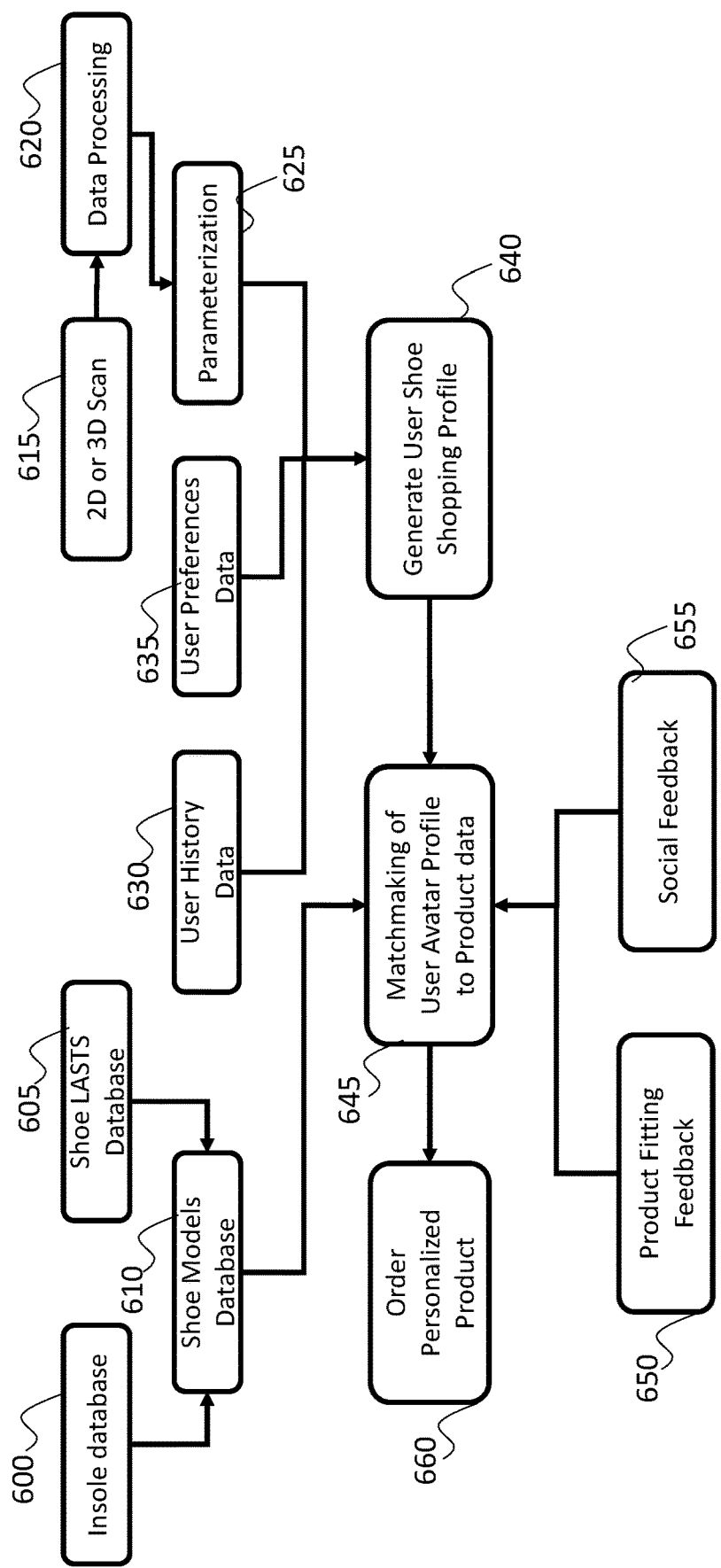
FIG. 6 is a flow diagram indicating an example of personalized shoes shopping, online or offline, according to some embodiments.

Reference is now made to FIG. 6, which is a flow diagram indicating an example of personalized shoes shopping, online or offline, according to some embodiments. As can be seen in the figure, insole information from an insoles product database may be acquired at 600. In addition, shoe last information from shoe lasts product database may be acquired at 605. In some cases, inner sole data, shoe last data and/or shoe model data may include data about each product's shape, volume, materials of shoes, closure type, shoe type, width, length, height, thickness, elasticity of materials, comfort fit etc. In some examples, mesh analysis and digitization may be provided, for example, to run a mesh analysis of each 3D last, combined with 2D DXF data, to be added to shoe last database 605. In addition, shoe model data for shoes to be discovered, purchased or manufactured may be acquired from shoe models database 610. In some cases, for example, 3D STL files may be imported for shoe lasts, and 2D DXF files may be imported for last bottoms.

At step 615, scanned or geometrical data may be acquired for a user, for example, from standard photographs, 2D and/or 3D image scanning, or from capture and processing using an automated shopping assistant apparatus etc. This graphic data may be processed at 620, by the personalized shopping system, over the cloud or in the unit itself, in order to generate a user's physical profile based on the user's physical properties. The profile may include all or some of the following attributes: a 3D mesh including the exact geometry of the profile, a 3D mesh including the exact geometry of one or more parts of the user's body, 2D images, properties calculated from one or more of the input methods, including specific volumes, cross section measurements, specific distances and lengths, as well as non numeric attributes such as preferences etc. For example, a user's foot or both feet together may be pictured or scanned while standing on the floor or on another other surface, on or near a reference object, etc. Further, the user's foot or feet may be scanned by the camera scanning around the different angles of the feet, or by the person moving around the camera, thereby generating a 3D model, a movie or a series of pictures as reference. The scanned data may typically be processed, optionally including interpolation and/or cleaning, to allow for object identification and mesh generation, or other suitable processing means. In some cases, meshing may further enable removal of excess geometries and/or fixing of mesh errors, for example, including separation, identification and preparation of each of the feet, removal of the floor, pants or other excess materials from the scans etc. Scanned data processing may, in some cases, allow for feet alignment, which also helps separation or individualization of the two feet, to provide accurate measurement of both feet, including dimensional analysis to determine general and area specific lengths, width and height, and Cross sectional analysis to determine area, perimeter, and other dimensions at specific cross sections. Scanned data processing may allow for smoothing of the edges of the scanned feet, building of missing volumes, constructing of the soles of the feet etc. In some cases, full foot volume and/or area specific volume may be extracted from the model as additional information. At step 625 the processed user scanned data may be parameterized, for example, to extract precise length, width, height, arch, ball, cross section, circumferences and volume dimensions etc. These parameters may be calculated off the clean 3D mesh using specific algorithms. For example, the calculation of the foot arch height off a model that was scanned in the standing position is complex and may be based on comparison of XYZ parameters of various anatomical parts throughout different cross sections in the center of the foot. The width of the foot may be calculated based on the volume of the toe box calculated both at a 3D mesh and 2D cross section level. The length of the foot may be calculated from a combination of the total length and the "ball length" which represents the distance between the heel of the foot and the 1st metatarsal. In addition, user specific conditions, such as sores, infections, damage etc. can also be identified and integrated into the user's shoe shopping profile. At this step, the pronation or supination condition of the foot may also be analyzed. Additionally, the arch of the foot may be identified and measured for fitting of support insoles or other prosthetics.

At step 630 history data for a user may be retrieved, for example, based upon previous user purchases in a store or chain of stores, whether from online and/or in store experiences. At step 635 user preference data may be acquired, such as size, color, material, type preferences etc. At step 640 a multi-dimensional user shoe shopping profile, hereinafter referred to as a user shopping avatar, may be created, by processing the various input data from steps 615, 620, 625, 630 and 635, thereby generating a user shoe shopping avatar or profile that includes user physical properties as well as user behavior and user preference data. In some embodiments the user shoe shopping profile includes both feet of the user, which are typically different and for which parameters are determined individually, thereby benefitting from individual profiles for left and right feet.

At step 645 a matchmaking of the user shoe shopping profile to shoe products being examined, researched or required is executed. At this step, the product data including dimensions, from product databases 600, 605 and 610 is matched to products being researched by a user, in accordance to the specific user shopping profile, thereby enabling advanced filtering out of non appropriate products for the specific user, and the advanced matching up of appropriate products, in accordance with the specific user's personal shopping profile and preferences. The step of matching may be complemented by a provision of recommendations for the user, based on the above profile to she matchmaking process. This step may use the models of the foot and shoe digital profiles directly, and/or the parametrized numeric model.

At step 650 product fitting data from feedback of physically present personnel or remote people may be used to help modify the matchmaking of user data to product data, for example, the feedback from a salesperson in a store may be used to update the user profile, or the feedback from remote people connected via a smart phone or computer for example. In some cases, for example, salesperson or friend feedback, such as which colors look good on a person or which size looks best etc. may be used by the user to update their shopping profile. In some cases, advanced graphic processing and 3D rendering may be used for the user to try on the product being researched, such that the user may see themselves virtually dressed in the product in accordance with a digital simulation that places the product onto the user shopping avatar. As above, the user may use the shopping Avatar to provider further feedback to modify the user's shopping profile. At step 655 feedback may be acquired from social networks to which a user is connected, to help modify the user shopping profile.

At step 660, a personalized pair of shoes may be ordered by a user, whether inside a physical store or in an online store. Further, a personalized product may be ordered from a manufacturer who may produce a product based upon the user's request such that the product is a once-off customized product for a user. Customized footwear based on this invention may be customized and/or personalized, for example, in of one or more of the following ways: shape (e.g., size, length, geometry, volume), design (e.g., colors, patterns, print, materials) or any other specification or combination of the above.

Figure 7:
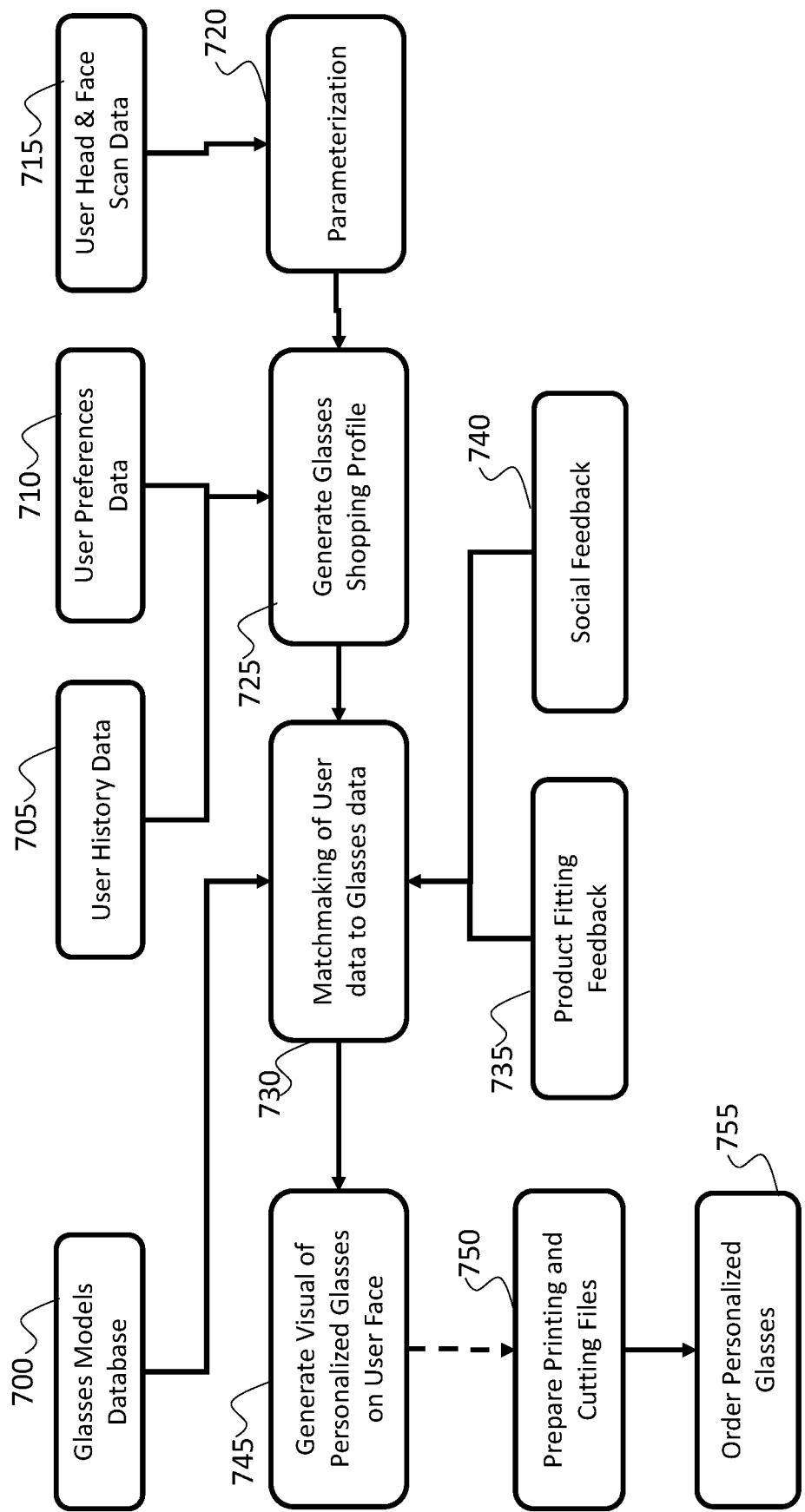
FIG. 7 is a flow diagram indicating an example of personalized eyewear shopping and manufacturing, online or offline, according to some embodiments.

Reference is now made to FIG. 7, which is a flow diagram indicating an example of personalized eyewear shopping and manufacturing, online or offline, according to some embodiments. This embodiment refers to both sun glasses and any type of optical glasses. As can be seen in the figure, glasses models information from glasses product database may be acquired at 700 from a glasses models or products database of various file types or data structures. According to some embodiments, glasses frame acquisition may be enabled by preparing parametric models, for example, by generating model parameters for multiple to input types, handling resolution adjustment, enabling automatic rigging and skinning, integrating range of motion animation and corrective shape-keys etc.

At step 705 history data for a user, for example including facial anatomical landmarks and measured distances such as inter popular distance, location of each eye, cheek, temple, and various points on the ear and the nose etc., may be used. The general parameters of each face are also loaded, optionally including the volume, proportions and standard shape, may be retrieved, for example, based upon previous user examinations and/or purchases in a store or chain of stores, whether from online and/or in store experiences. At step 710 user preference data may be acquired, such as size, color, material, type preferences, usage needs etc. This data may be acquired directly or indirectly, for example, using purchase information, questionnaires, forms and/or any other data acquisition method.

At step 715, scanned or graphic data may be acquired for a user, for example, from standard photographs, 2D and/or 3D image scanning, or from capture and processing using an automated shopping assistant. This includes, for example, any type of 3D scanning technology, as described in the above section or alternative 2D method using or not using reference objects for sizing. Typically, user head and face scan data may be acquired at this stage. In some embodiments, head and face model preparation and analysis may include model preparation such as smoothing and cleaning, rebuilding of the mesh with enhanced topology and/or optimized detail/weight ratio compression for optimal display in real-time, and/or orientation and alignment. Further, facial feature recognition may be used, for example, to generate a facial model rendered from multiple angles (e.g. 3 to 15 angles, to help determine Normal, Depth, Color). Moreover, computer vision and/or machine learning algorithms may be applied, for example, to identify the Eyes, nose, nose bridge, temples, ears etc. The processing of the scanned data may further include projection of 2D Landmarks to the 3D Model, and validation of anatomical landmarks. In the case of absent landmarks, an assessment based on statistic or empiric results may apply for replacement of these landmarks.

At step 720 the processed user scanned data may be parameterized, for example, to extract the precise face length, width, height, proportions, nose width and volume, ear size, ear height, ear position, skin color, and/or other relevant facial characteristics and dimensions etc. This data may be processed by the personalized shopping system at 725, together with the user history data from 705 and user preferences data at 715, to generate a user's glasses shopping profile based on the user's face profile and other physical properties, as well as user behavior and user preference data. In some embodiments the user glasses shopping profile includes both eyes of the user, which are typically different, thereby benefitting from individual profiles for left and right eyes. In some embodiments the optical prescription will be collected using a picture, an e-form, or an embedded testing method inside the application, or in some cases from external prescription files. According to some embodiments, the system may recommend specific models based on the face shape, previous purchases and history and optionally based on a comparison (optionally anonymous) to similar avatars.

At step 730 a matchmaking of the user glasses shopping profile to the glasses products being researched or required is executed. At this step, the product data from product database 700 is matched to products being researched by a user, in accordance to the specific user shopping profile, thereby enabling advanced filtering out of non appropriate products for the specific user, and the advanced matching up of appropriate products, in accordance with the specific user's personal shopping profile and preferences.

At step 745, each frame is adjusted to fit on a user's face using frame Customization, that may include, for example: Taking key measurements on a subject or user's face; applying iterative comparison algorithms to adjust the frame to the face; digitally positioning the frame on the subject's face, orienting the frame appropriately to the face, scaling nose bridge size, width and position, adjusting arm folding, arm Length and pentoscopic tilt or angle, in accordance with the subject's face, as per the prepared user glasses shopping profile or avatar, etc.

At step 735 product fitting data from feedback of physically present personnel or remote people may be used to help modify the matchmaking of user data to product data, for example, the feedback from a salesperson or optometrist in a store may be used to update the user profile, or the feedback from remote people connected via a smart phone or computer for example. In some cases, for example, salesperson or friend feedback, such as which colors look good on a person or which size, style, type looks best etc. may be used by the user to update their shopping profile.

In some embodiments, at step 745, advanced graphic processing may be used for the user to virtually try on the product being researched, such that the user may see themselves dressed in the glasses in accordance with a digital simulation that places the glasses onto the user shopping avatar's face. The virtual try-on may, in some embodiments, include features such as physical simulation that positions the glasses at the correct or optimal position and can slide these along the nose. In addition, the try-on may include an overlay of a picture or 3D model on top of the face model/or a series of pictures or any combination of the above. Animated effects may be included to emphasize the different attributes of the glasses including customization animation in the case of custom frames, or other animation such as fly in/fly out animation for switching between pairs. As above, the user may use the shopping Avatar to provider further feedback to modify the user's shopping profile. In some embodiments, the user may view the customized frame on a digital version of his/her face, to provide profound visual feedback. For example, the user's face may be shown in a 3D viewer and the appearance may be enhanced, so as to provide one or more of 3D view manipulation (eg. zoom, rotation), and animated effects to compliment user experience, such as a breathing face, smile, blinking or other animated or static visual effects. Further, the user may thus be provided with customization options including choosing any frame from the collection, customizing the frame and lens colors, customizing an automatic recommended fit, personalization of a file (e.g. text, prescription etc.), and enabling side-by-side comparison between different frames. At step 740 feedback may be acquired from social networks or to which a user is connected, to help modify the user shopping profile Of course, other steps of combinations of steps may be used to process the input data.

Step 750 refers to an embodiment in which the system enables production of custom eyewear based on automated or semi-automated parametric design of the frame to fit the user. At step 750 relevant glasses production printing and cutting files may be prepared by the system, if necessary. In some embodiments, 3D printing files of standard forms for examples STL or OBJ and 2D lens cutting files such as DXF etc. may be prepared. In some embodiments the system creates two or more pairs of models for each of the frame designs. This allows, for example, for a light weight model to be used for visualization purposes on the frontend of the application while maintaining a high resolution model for the printing file preparation, that may include, for example, high resolution features and details, such as hinges, grooves, angles, ear pieces etc. The eyewear customization of print models described herein may be automatic and/or manual. Further, the file preparation for 3D printing may include automatically fixing of printability issues, generation of normal, duplicates, holes and non-manifold geometry etc. In some embodiments the system may create custom tags, labels, or other product identification or recognition technologies or devices, on the glasses or eyewear, for example, including text, QR or barcode that would allow traceability throughout the production and distribution process.

At step 755, a personalized pair of glasses may be ordered by a user, whether inside a physical store or an online store. Further, a personalized product may be requested from the store, or ordered from a manufacturer who may produce a product based upon the user's request such that the product is a once-off customized product for a user.

According to certain embodiments, a system and process are described for automated personalized product ordering using a digital mirror or personalized viewing protocol. This embodiment may integrate virtual reality and/or augmented reality to manipulate, view and/or try on designated equipment such as existing or designed glasses, on a screen, table, smartphone, communications device etc., to allow visual representation of the custom or non-custom frames on the face of the client.

According to certain embodiments, a file format adapted to enable personalized product ordering is provided. This file format incorporates all of the relevant information, including physical properties and personal preference, to represent a user and help the user perform personalized custom or non-custom shopping for clothing, eyewear, footwear, or other body related products. This avatar standard format may be used to plugin into substantially any shopping platform, online or physical, to allow customization of the store to fit the physical and aesthetics needs and preferences of a customer.

Reference is now made to FIGS. 8A-8G, showing different views of a POS apparatus, Launchpad or kiosk, according to some embodiments. In some embodiments, the shopping assistant apparatus generates a user avatar based on one or more of 3D scanning, image acquisition using one or more cameras, measuring a user profile with pressure plates, etc. In some embodiments, a standing pad may be used to function as a positioning pad or reference for a user to stand on to perform a body scan. In some cases the standing platform may include lighting at the bottom of the standing pad, to support acquisition accurate measurement of any colors from cameras or scanners on the apparatus, by minimizing or marginalizing shadows, and causing a black/white perimeter effect. In some embodiments there may be a proximity sensor for each foot—to measure if the feet are in place or close, and tell the user to move if necessary. Further, the apparatus may include a distance or proximity sensor/robot that recognizes approaching user to attract the user to the apparatus, in which case the apparatus may be automatically started when a user enters a selected geographical zone. In further embodiments, a sensor may be used for measurement of the height of a user's instep—to establish instep volume, for example. In still further embodiments, specialist sensors may be used, for example, sensors to measure diabetes sores etc. Such sensors, such as cameras, 3D sensors, all around cameras, and or multiple cameras may be used.

Figure 8A:
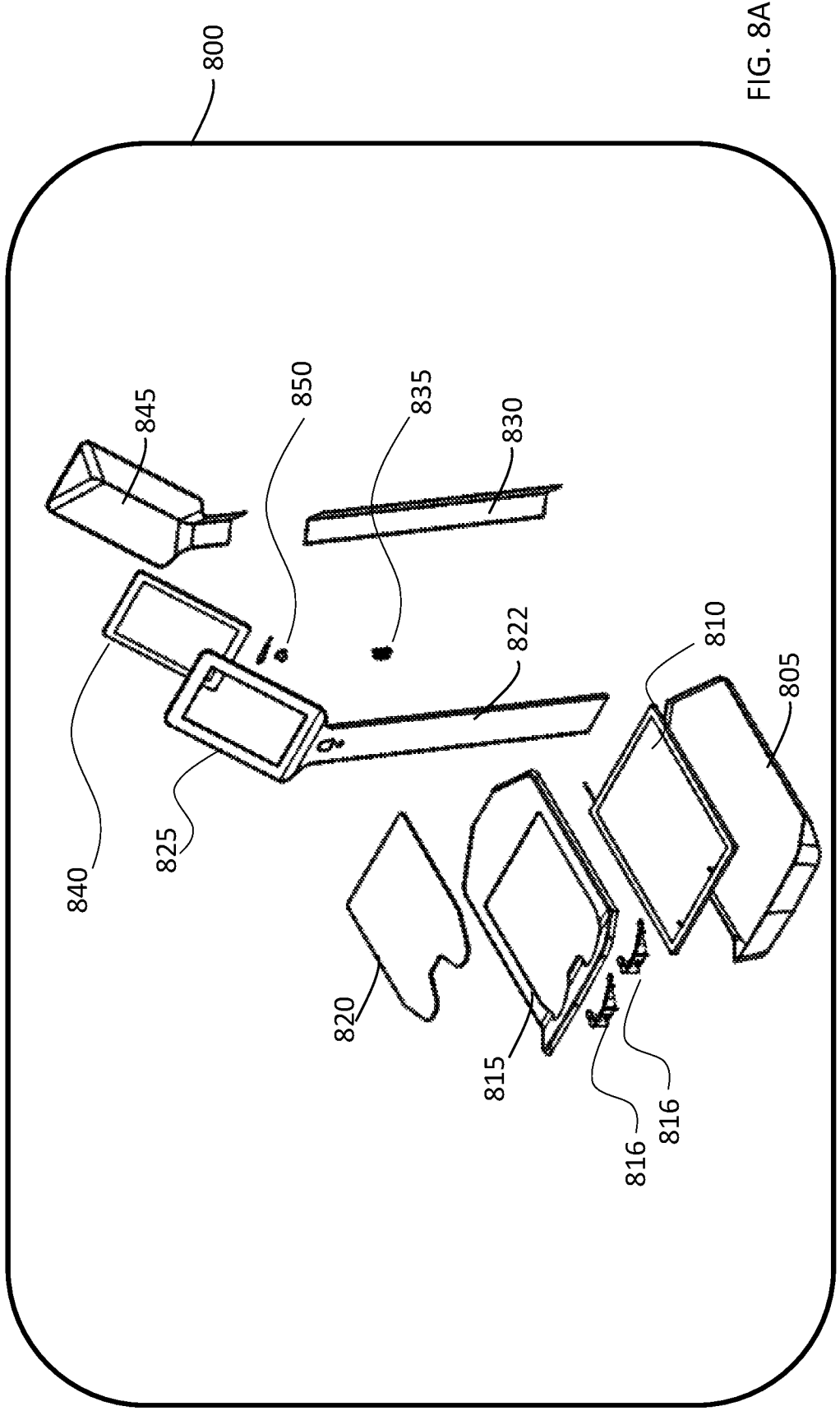
FIG. 8A shows an exploded view of an example of a shopping assistant apparatus, according to some embodiments.

FIG. 8A is an exploded view of an example of the components of the POS apparatus or Kiosk device, in some embodiments. As can be seen, the kiosk device 800 may include a standing base 805, a light source for optionally lighting the standing base, proximity sensor(s) 816, for identifying the positioning of feet to be scanned by kiosk device 800, a standing pad 815, with space for standing on with both feet, and a pad layer 820, on which the feet are mounted on. In some embodiments pad layer 820 may be integrate a pressure sensing mechanism, such as flat bed scanner; plate of pins; pressure plate; touch screen type surface with a capacitor and/or pressure sensor element etc., to determine foot arch dimensions. In some embodiments, arch dimension measurement element(s) may be used to determine a need for and/or dimensions of an inner sole(s) for a user.

In some embodiments, arch dimension measurement element(s) may be used to determine a need for and/or dimensions of a user's instep profile.

In some embodiments, arch dimension measurement element(s) may be used to determine a need for and/or dimensions of a user's ball (of the foot) profile.

In other embodiments one or more lasers or other lighting mechanisms may be used to determine foot arch, ball, or in step dimensions. In one example, a laser from above the foot may be used to show the height or arch and also size of a bridge of the foot, for example, by identifying the size of the "hidden" area not seen by laser, and using the "hidden" space to determine parameters such as height, at different points on the foot. In a further example, diffraction grating, prism, or other filters to use multiple lines to be able to identify highest point of foot.

In still further embodiments, one or more lights, optionally of different colors, separately and/or in combination, may be used, together with image processing to neutralize a color of a sock and/or foot, and help identify non-foot space, In other embodiments one or more may be identified with the arch of a foot, for example, using a background elimination technique.

Further, kiosk device 800 may include a main body 822, including a computer holding stand 825, and a camera holding element 826, for holding one or more camera elements 835, a panel element 830, a further panel or cover element 845, a computing screen, preferably a touch screen PC or tablet 840, and optionally having a place for setting up a proximity sensor 850, for example, for identifying a user proximity to the computing device.

Figure 8C:
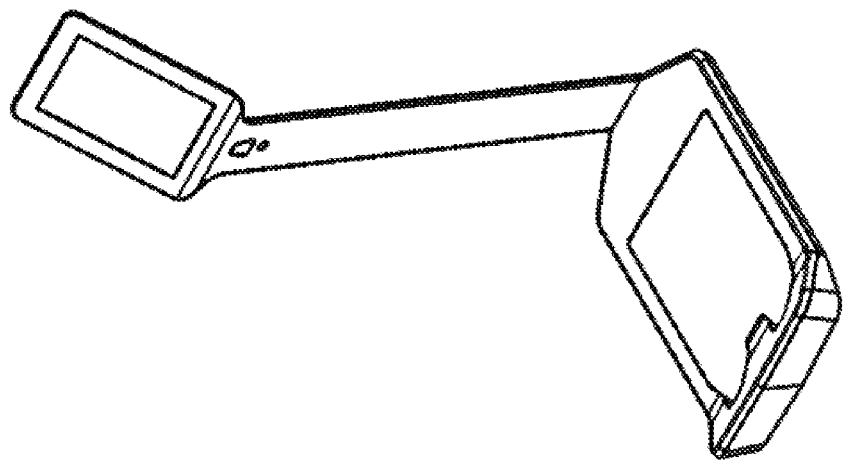
FIGS. 8B-8H show a set of views of an example of a shopping assistant apparatus, according to some embodiments.
Figure 8B:
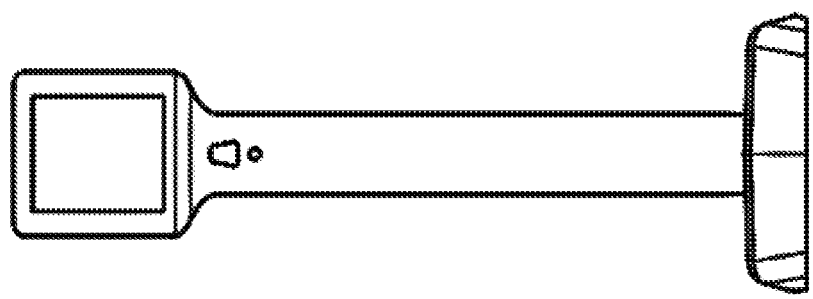

FIG. 8B is a front view of an example of the POS apparatus or Kiosk device.

FIG. 8C is an isometric view of an example of the POS apparatus or Kiosk device.

Figure 8E:
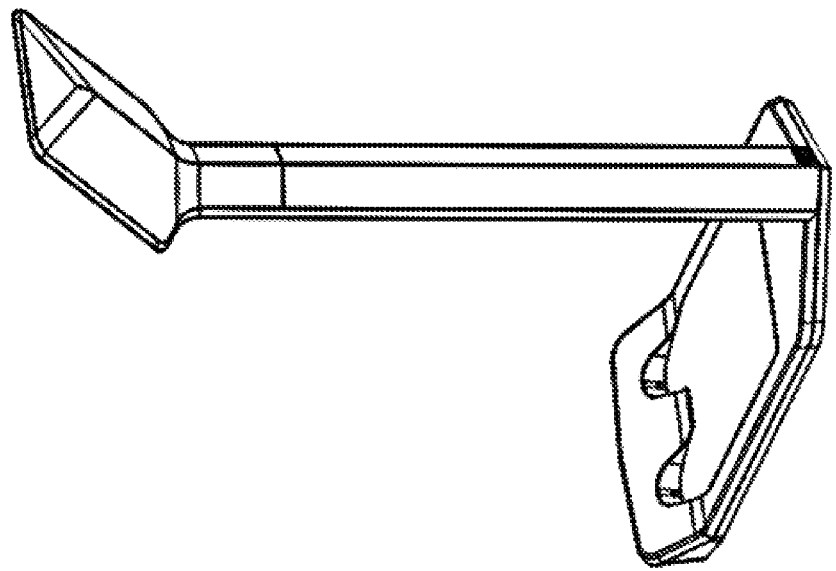
Figure 8D:
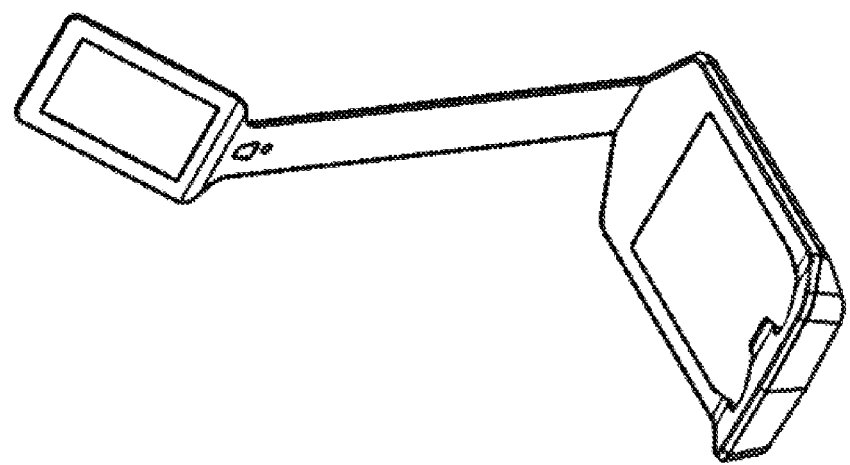

FIG. 8D is an isometric front view of an example of the POS apparatus or Kiosk device.

FIG. 8E is an isometric back view of an example of the POS apparatus or Kiosk device.

Figure 8G:
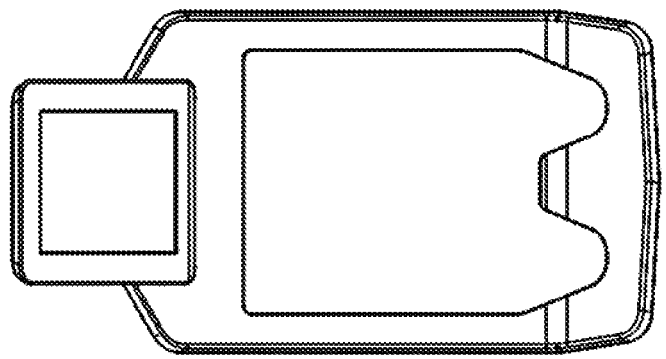
Figure 8F:
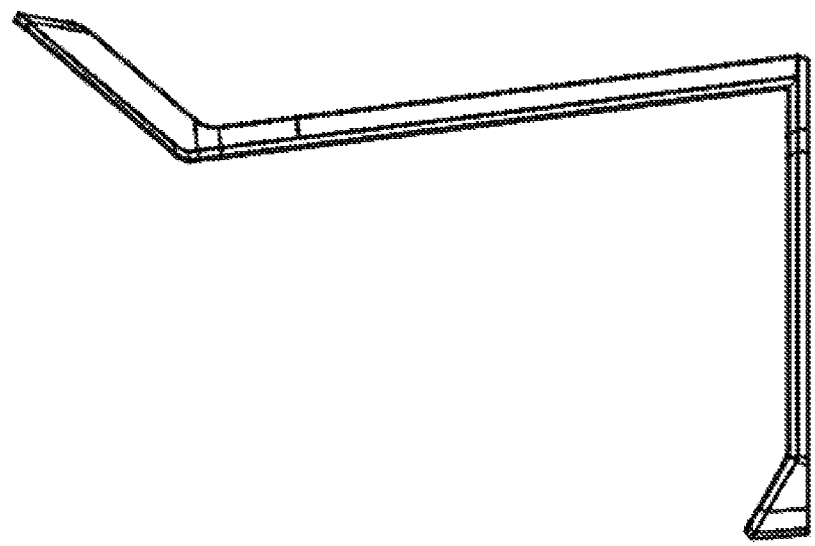

FIG. 8F is a side view of an example of the POS apparatus or Kiosk device.

FIG. 8G is a top view of an example of the POS apparatus or Kiosk device.

Figure 8H:
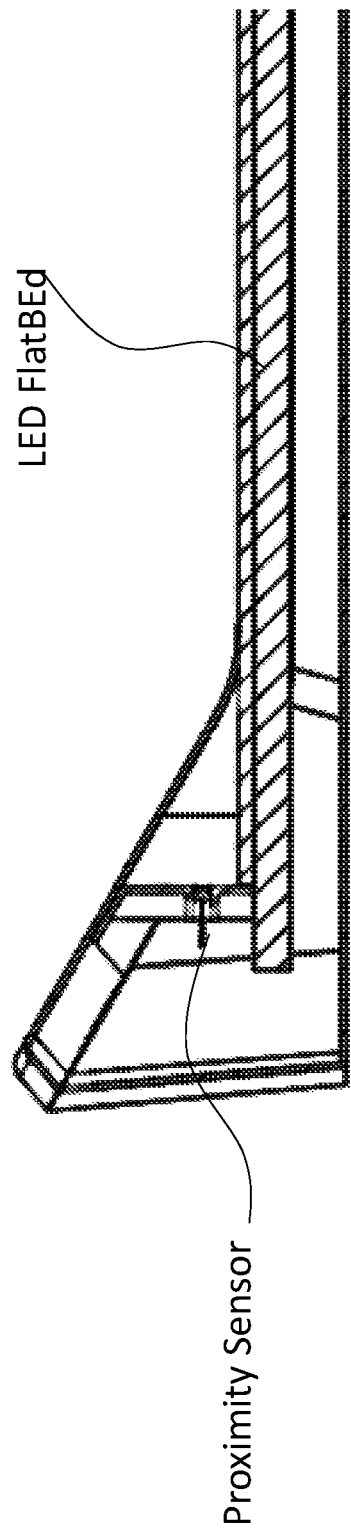

FIG. 8H is a view of an example of one or more sensors in POS apparatus or Kiosk device. As can be seen, the kiosk device, multiple sensors may be configured, for example, one or more proximity sensors, a LED Flatbed may be configured for providing a light source from under the standing area.

Figure 9:
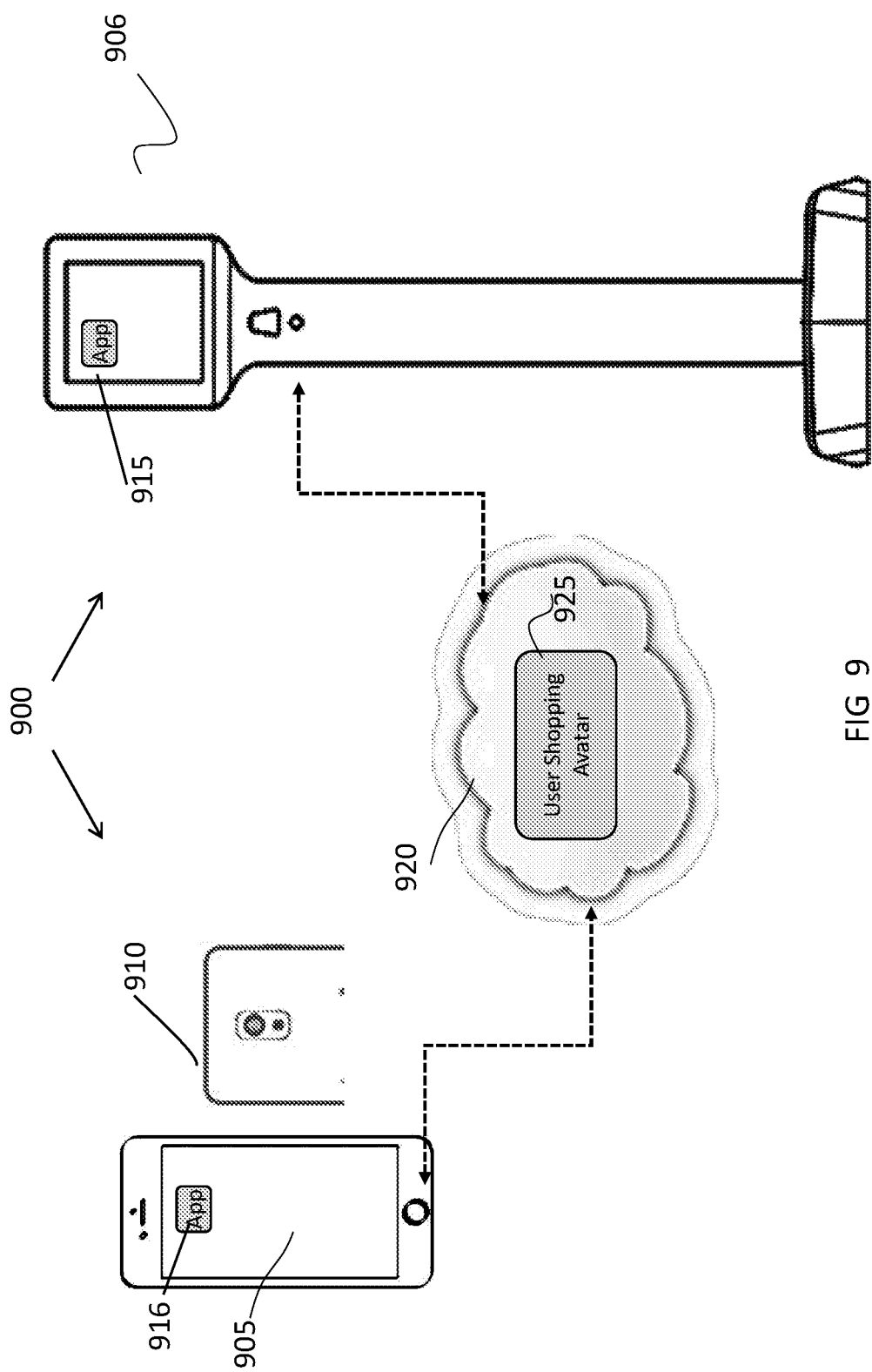
FIG. 9 shows a shopping assistant system, according to some embodiments.

Reference is now made to FIG. 9, which shows a schematic view of the shopping assistant system 900, including automated shopping assistant apparatus 906, which integrates a computing component adapted to run a shopping assistant Application or software program 915. Automated shopping assistant apparatus 906 is adapted to connect to a communications network, such as communications cloud 920, to access the user shopping profile 925, if on the cloud, and/or transmitting the user shopping profile to the cloud. Further, a remote user mobile device, such as a smart phone, tablet or other camera supporting mobile communications device 905, 910, according to some embodiments, which are adapted to run a shopping assistant Application or software program 916. Devices 905 and 910 typically include one or more cameras 910, for example to enable capturing information about a person's foot or both feet optionally simultaneously using a standard picture/scan, video, series of pictures or advanced sensing components such as structured light, time-of-flight or others in IR/NIR or visual light conditions. Devices 905/910 typically include a gyrometer to provide camera orientation data to the device camera, for example, to only allow a picture to be taken when the camera is substantially flat. In some embodiments, internal sensing components and/or additional sensors may be attached to the communications devices 905, 910 to supply supplementary data to the system. For example, such sensors may assist in improving accuracy of measurements, assisting the user during the capturing of the data with real-time feedback, and/or providing input to the calculation engine. Remote devices 905 and 910 may communicate with communications cloud 920, and in particular, may be connected to the device user's digital shopping avatar or profile 925. In some embodiments, a user may generate the shopping profile using the mobile device 905,910, for one or more users, in addition to or in place of the automated shopping assistant apparatus 906

Figure 10:
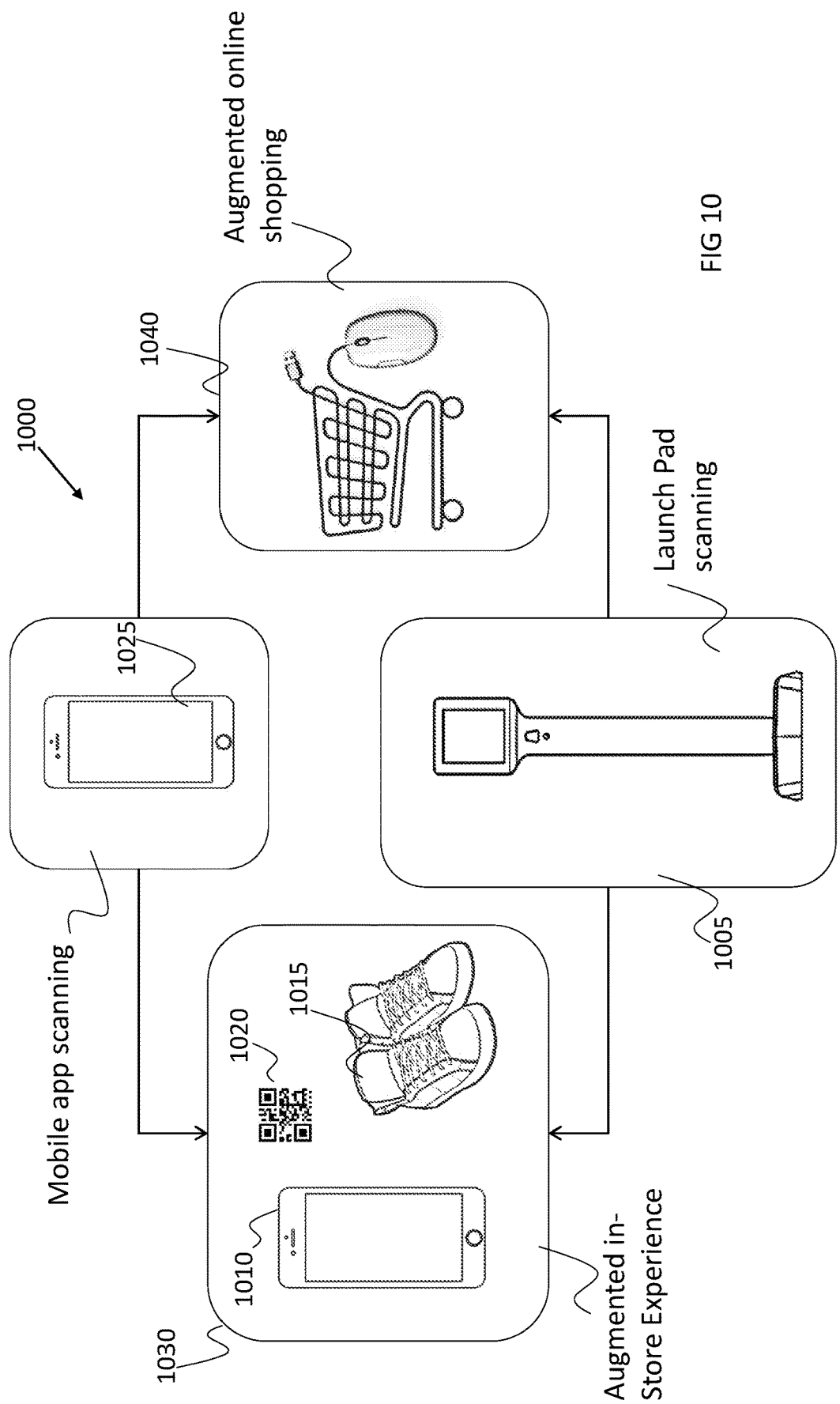
FIG. 10 is a flow diagram indicating an example of integrated usage of a shopping assistant in store apparatus, and a remote user communications device with a personalized shopping support application, according to some embodiments.

Reference is now made to FIG. 10, which shows a schematic view of the shopping assistant system 1000, and the work flow between the components. As can be seen, the launch pad or shopping assistant apparatus 1005 can scan a user, for generation of a shopping profile for the user. The generated profile is sent to the user's mobile device 1010, and can subsequently be used for scanning products, such as shoes 1015, optionally via a product tag, such as QR code 1020, representing the selected product. Further, in some embodiments, the user may build a shopping profile using a mobile Application 1025. In some embodiments the user shopping profile can be used to augment in store shopping, at 1030. In some embodiments the user shopping profile can be used to augment online shopping, at 1040.

Figure 11A:
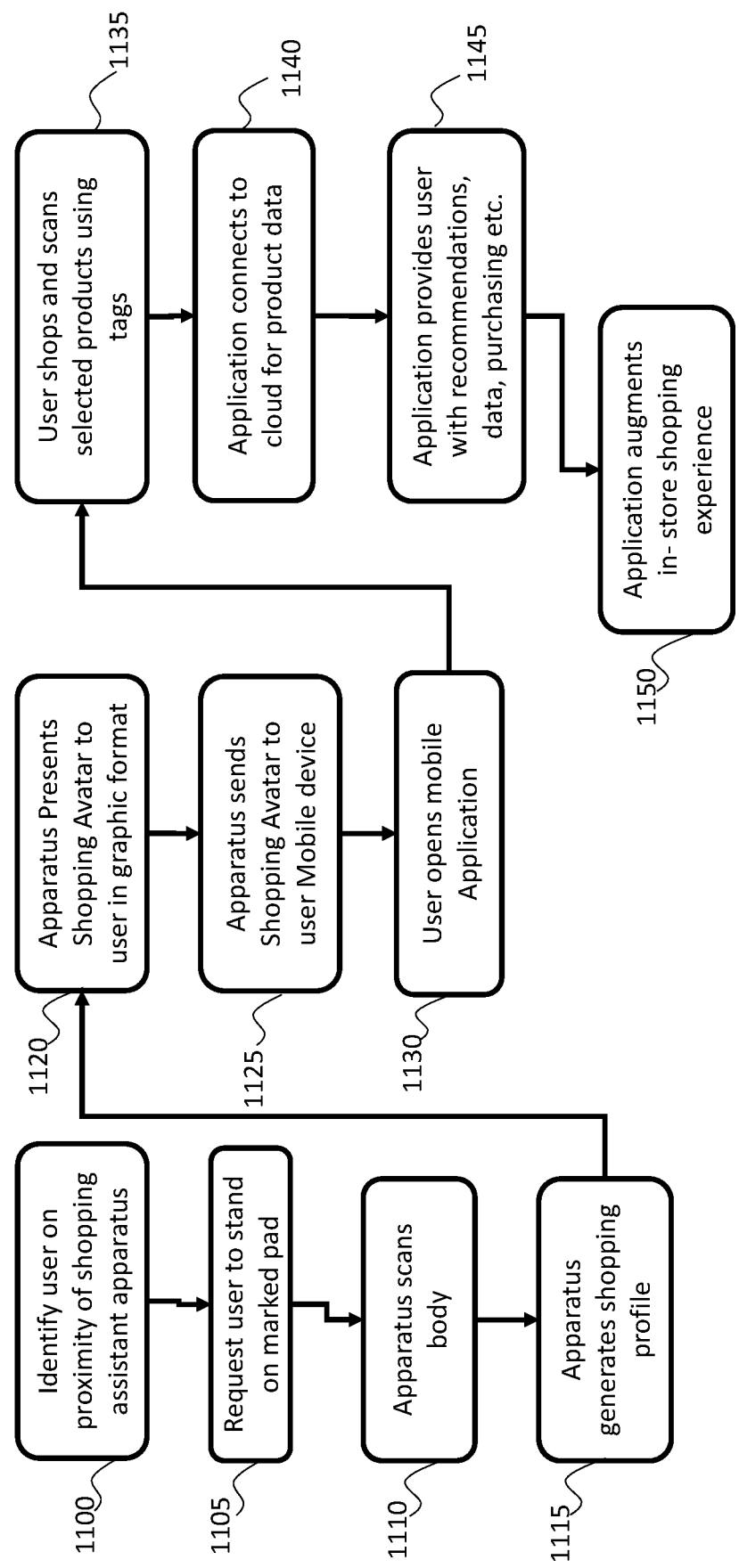
FIGS. 11A and 11B describe examples of a process of shopping assistant usage, according to some embodiments.

Reference is now made to FIG. 11A, which is a flow diagram indicating an example of personalized footwear shopping in a shopping store using an in store or POS automated shopping assistant apparatus, in combination with a mobile computing device application. As can be seen, at step 1100, a user may be identified via a proximity sensor of a shopping assistant apparatus, and at step 1105 the user may be requested to stand on the marked pad, and optionally provides interactive guidance to make sure the user stands in the correct position to enable accurate scanning. At step 1110, the apparatus scans the body or body parts/elements, and at step 1115, generates a shopping profile based on the scan. At step 1120 the apparatus may present the shopping avatar to the user in a graphic format. At step 1125 the apparatus may send the shopping avatar to the user's mobile device. At step 1130 the user may open a shopping application that may use the application to assist with shopping and/or research. At step 1135, the user may use the avatar on their mobile device to shop or do research, for example, by scanning selected products using product identifier or recognition devices or technologies, for example, using coded tags, QR codes or barcodes. In general, the scanned products may be processed in a way that relates to the user avatar, for example, to determine if the product will fit the avatar, suits the user's profile or preferences etc. In some cases, the application may provide a graphic simulation of the selected product on the avatar. At step 1140 the application may connect to a communications cloud or other data base, to match the selected product(s) with product data, for example, to help determine purchasing options, inventory status, product qualities, product features, reviews, sizes etc. In some cases, at step 1145, the application may present the user with recommendations, purchase data etc. In still further steps, the application may augment the in-store shopping experience, for example, by providing shopping advice, options, shortcuts, access to additional databases etc.

Figure 11B:
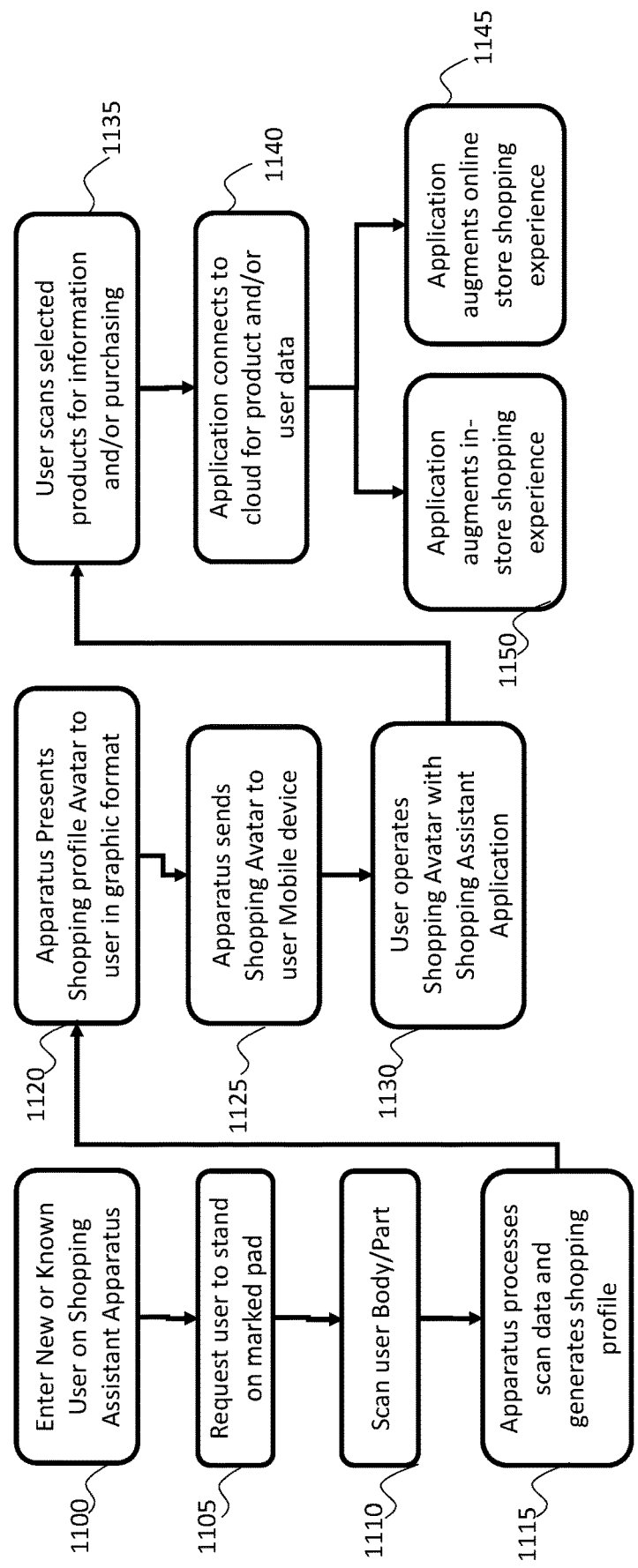

Reference is now made to FIG. 11B, which is a flow diagram indicating an example of personalized footwear shopping in a shopping store using an in store or POS automated shopping assistant apparatus, in combination with a mobile computing device application. As can be seen, at step 1100, a new or known user can be entered on the shopping assistant apparatus—for example, via a biometric identifier, entry screen etc. At step 1105 the user may be requested to stand on the marked pad, and optionally provides interactive guidance to make sure the user stands in the correct position to enable accurate scanning. At step 1110, the apparatus scans the body or body parts/elements, and at step 1115, processes the scan data and generates a shopping profile based on the scan. At step 1120 the apparatus may present the shopping profile as a simulation, shopping avatar or other virtual assistant, to the user in a graphic or other format. At step 1125 the apparatus may send the shopping avatar to the user's mobile device, in a format or configuration usable by the device's software, code or application(s). At step 1130 the user may open a shopping application or other program that may operate the shopping avatar with a shopping assistant application. At step 1135, the user may use the avatar on their mobile device to shop or do research, for example, by scanning selected products using a product identifier such as coded tags, QR codes or barcodes. In general, the scanned products may be processed in a way that factors in the generated shopping avatar, for example, to determine if the product will fit the avatar, suits the user's profile or preferences etc. In some cases, the application may provide a graphic simulation of the selected product on the avatar. At step 1140 the application may connect to a communications cloud or other data base, to match the selected product(s) with advanced product data, for example, to help determine purchasing options, inventory status, product qualities, product features, reviews, sizes etc. In other cases, at step 1140 the application may connect to a communications cloud or other data base, to match the selected product(s) with advanced user data, for example, to help determine user preferences, user history, user profile updates etc. In some cases, at step 1145, the application may present the user with recommendations, purchase data, purchase choices, reviews, news etc., to help augment the online store shopping experience. In some cases, at step 1150, the application may present the user with recommendations, purchase data, purchase choices, reviews, news etc., to help augment the in-store shopping experience, for example, by providing shopping advice, options, shortcuts, access to additional databases etc.

In some embodiments, the user shopping experience may be executed for additional users connected with a user of the shopping assistant. In such cases, the user application may contain shopping profiles of multiple users, thereby allowing the user of the mobile device to execute shopping for multiple users in according to the users' shopping profiles.

In accordance with some embodiments, mobile and/or user avatars may be shared with other users. For example, a user may have access to or control multiple user profiles, with the users' authorization, for example, in a wallet or holder of avatars or profiles. In such a case, the controlling user may shop on behalf of other users. For example, a parent may keep the profiles of all their family members, allowing the parent to easily shop online and/or offline for all the associated family members.

In accordance with some embodiments, additional personalization can be provided for each user mobile shopping avatar or user shopping avatar, such as an icon or picture. Such personalization may be particularly useful for a controlling user to manage multiple user or mobile shopping avatars. This information associated with any identifier may be saved on the cloud avatar database and associated with a user in any platform that s/he uses. For example, in the case where a family member scans and saves one or more of his or her family members profiles, these may be shared with another family member(s) who can now load them into an in-store system or a ecommerce website being used, and subsequently use this personalized information. In the case of a website, the output may be personalized in accordance to this personalized data and may even include the other user's picture or avatar or 3D model right next to the information provided, to reassure the user's confidence that the recommendations are personal and based on his or her profile, or other profiles being legitimately used by the user.

In accordance with some embodiments, an online store may include a user shopping virtual assistant, using a profile plug in or other digital object, that may appear on substantially any webpage (whether optimized for mobile phone, desktop, notebook, tablet, wearable etc.), when relevant, to offer recommendations, guidelines or other assistance to the user. For example, the virtual shopping assistant may show information about different fits for the user profile being used, or otherwise assist the user. For example, a user with a foot size of 41 European, while shopping or browsing in the Nike online store, may be informed that the equivalent size for their feet profile in Nike shoes is 42 European or US size 10.5. Additionally, if the user profile includes preference data, such as preferred colors and fits etc. the shopping virtual assistant may also provide suggestions or guidelines based on the user preferences. For example, in the Nike shoes store, the shopping assistant may suggest to the user to look for options that are 10.5 American size, in athletics shoes, in either blue or green, etc.

In some embodiments the virtual assistant may take the user directly to a page or pages that match the user shopping profile data and preferences. In one embodiment, the profile may direct the website into the sections that are interesting or relevant to a specific user while avoiding irrelevant pages. In another embodiments, the system may use the personalized information, alone or in aggregate with additional users, to rearrange the website and create a personalized version of the website that may represent what s/he may be most interested in and what would best fit for him or her.

In accordance with some embodiments, the virtual shopping assistant may enable rendering of 3D views of a product being viewed, and optionally of a personalized product. For example, a custom shoe being viewed in accordance with a user's shopping profile may be rendered in 3D from all sides and angles, to assist the user is viewing the product from multiple dimensions.

In accordance with some embodiments, a virtual fitting module may be provided, to allow dressing of the shopping avatar with the product(s) being viewed.

In accordance with some embodiments, a user shopping avatar may be a once off avatar for a store. In other embodiments the user shopping avatar may be applicable to a chain of stores. In other embodiments the user shopping avatar may be applicable to a variety of brands or stores, for example, all owned by a parent entity. In other embodiments the user shopping avatar may be applicable to any or all stores, via connecting to the universal user profile in the cloud.

Figure 12B:
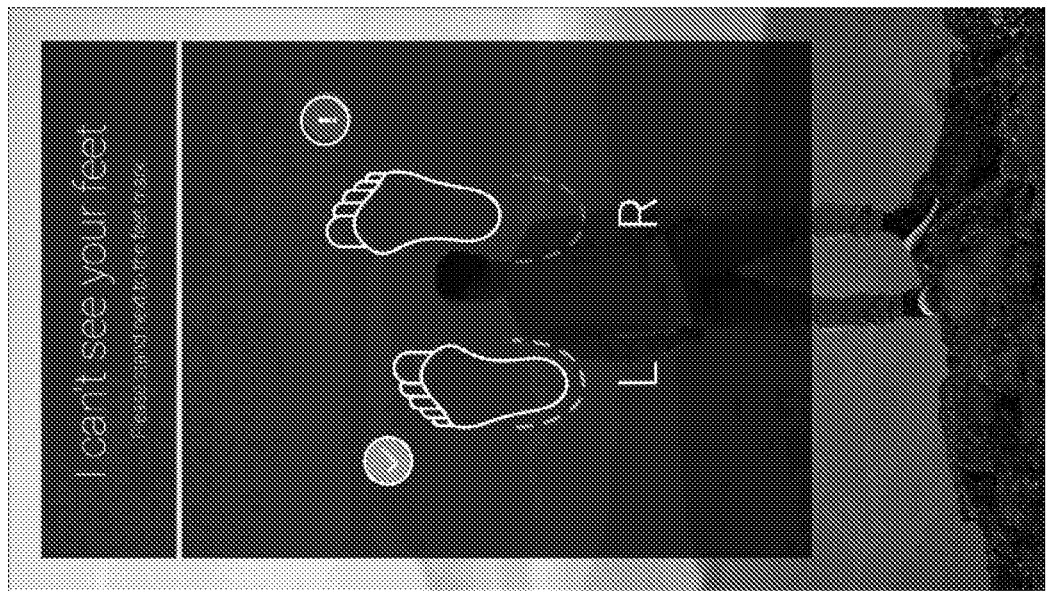
FIGS. 12A-12B are examples of screenshots showing interactive screens on the shopping assistant screen, for guiding a user to place their feet on the marked pad, according to some embodiments.
Figure 12A:
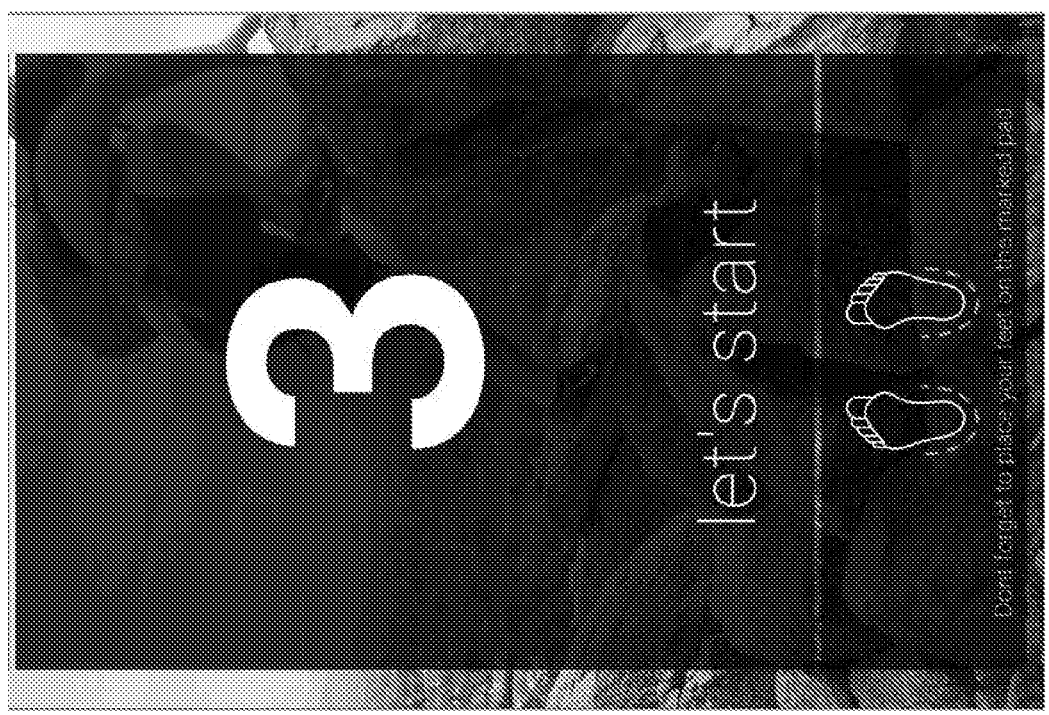
Figure 13B:
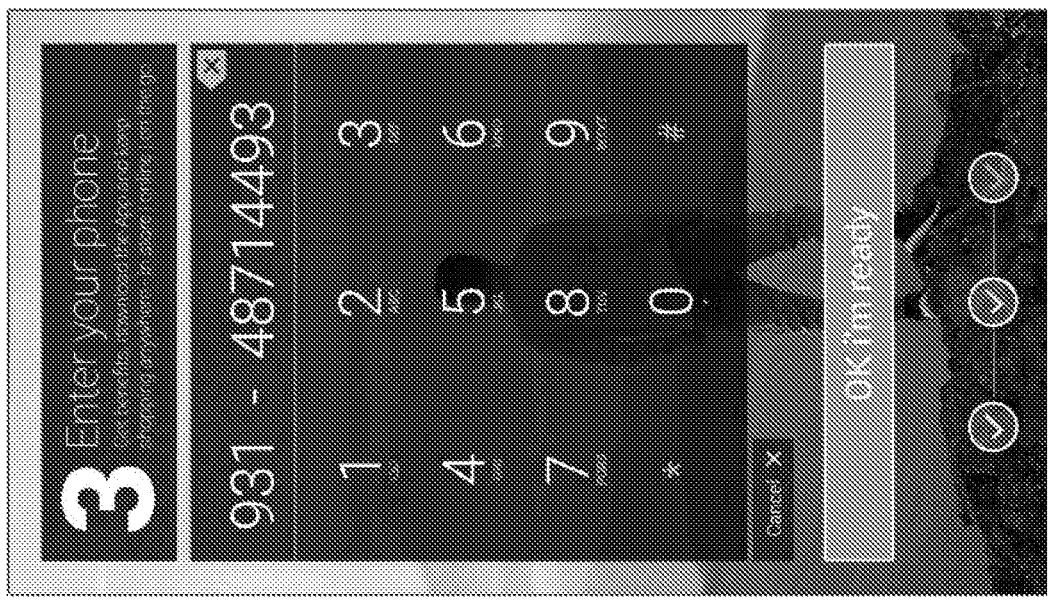
FIGS. 13A-13B are examples of screenshots showing an interactive guide on the shopping assistant screen or mobile screen, for helping the user to define their profile, and their contact information, according to some embodiments.
Figure 13A:
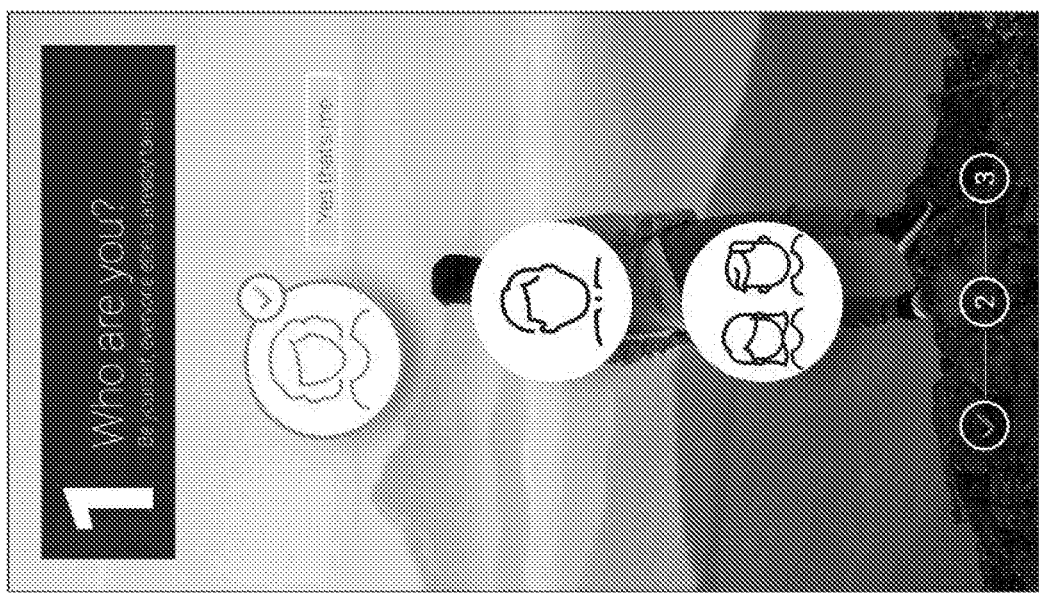
Figure 14B:
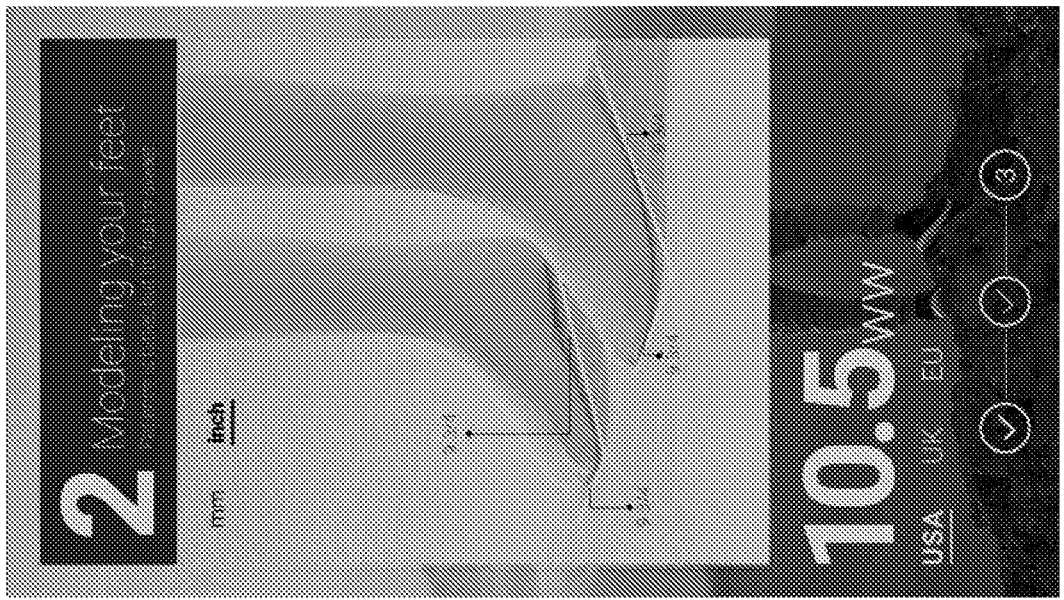
FIGS. 14A-14B are examples of screenshots on the shopping assistant screen or mobile screen, for showing a simulated rendition of a pair of scanned feet and lower legs, according to some embodiments.
Figure 14A:
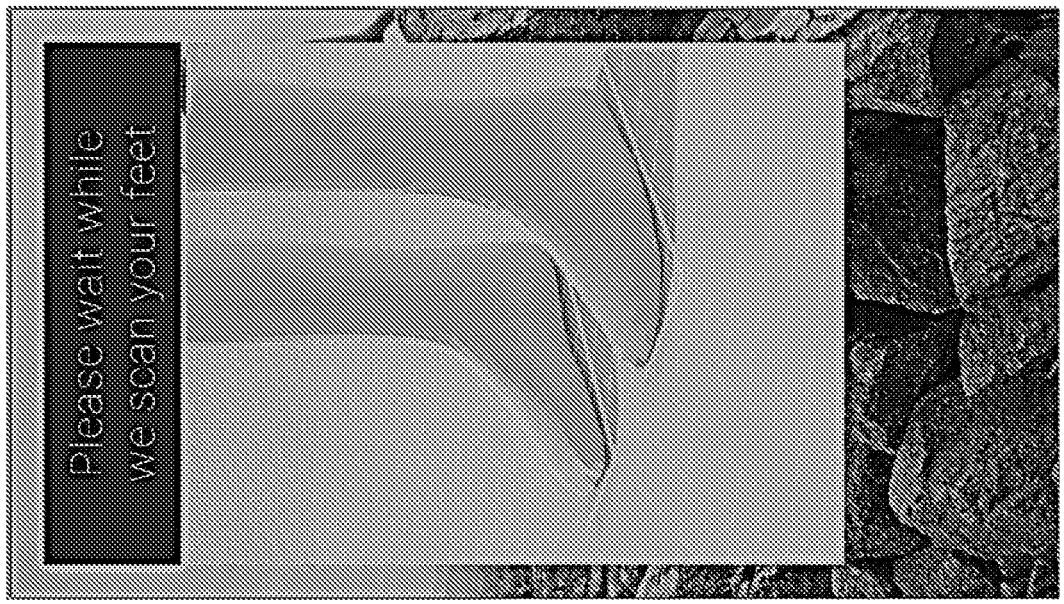
Figure 15B:
FIGS. 15A-15B are examples of screenshots on the shopping assistant screen or mobile screen, for assisting a user in entering behavior related information, that may be used to provide better user related output.
Figure 15A:
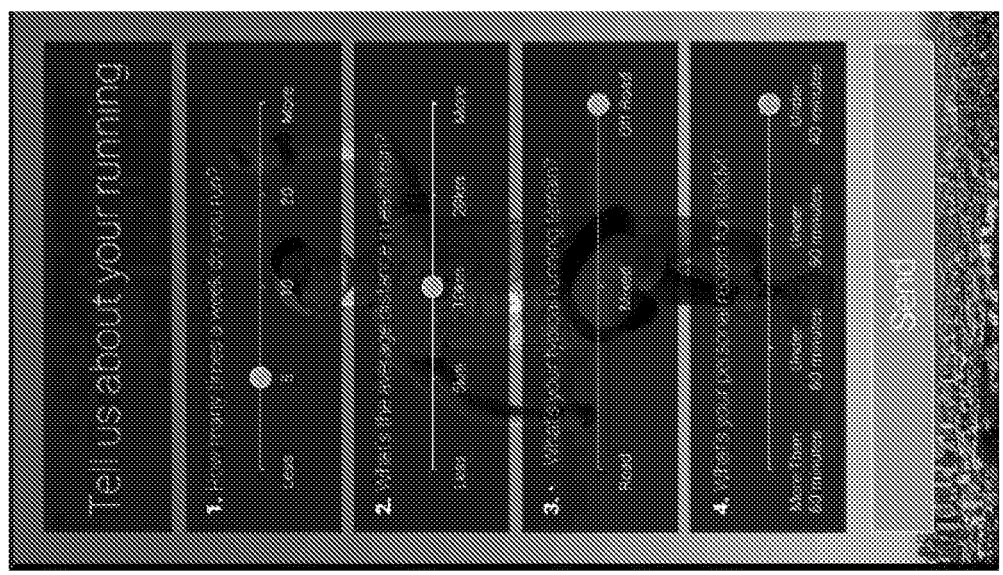

Reference is now made to FIGS. 12A-12B, which are examples of screenshots showing interactive screens of the shopping assistant screen, for guiding a user to place their feet on the marked pad, according to some embodiments;

Reference is now made to FIGS. 13A-13B, which are examples of screenshots showing an interactive guide of the shopping assistant screen or mobile screen, for helping the user to define their profile, and their contact information, according to some embodiments;

Reference is now made to FIGS. 14A-14B, which are examples of screenshots of the shopping assistant screen or mobile screen, showing a simulated rendition of a pair of scanned feet and lower legs, according to some embodiments;

Reference is now made to FIGS. 15A-15B, which are examples of screenshots of the shopping assistant screen or mobile screen, for assisting a user in entering behavior related information, that may be used to provide better user related output.

In some embodiments, the shopping assistant apparatus may help a chain store generate loyalty online and/or offline, by allowing automated shopping assistance in multiple stores, proactive up sales and cross sales, etc.

In one embodiment of the present invention, the user shopping experience for footwear may be substantially enhanced, by applying the following steps: Measuring on apparatus 185 a user physical profile, and providing a user standard size as well as modifications for different shoes/brands; Getting an ID or shopping profile of the customer to the customer's mobile computing or communications device; and getting an ID or shopping profile of the customer from apparatus 185 to a communications cloud.

In a first user case of the present invention, where a user has no previous user profile, the shopping assistance process may be implemented as follows: The user generally removes shoes and stands on the Launch pad or shopping assistant apparatus at entrance to a store or shopping areas. In the current example, a footwear application is described. The apparatus subsequently measures/scans the users body area, such as feet, and thereafter the apparatus, or cloud network, may process the user data and generate a user shopping avatar. Once generated the avatar is sent to the user's mobile device, running the shopping assistant Application, for example using mail, beacon, SMS, QR code, IR beam etc. The user may then scan wanted shoes, whereby the apparatus is configured to match and then try on shoes wanted to an avatar to provide best fit. The apparatus may also provide to the user related product information, such as availability, colors, sizes, related shoes, rankings etc.

In a second user case of the present invention, where a user has multiple devices, the shopping assistance process may be implemented as follows: The user generally removes shoes and stands on the Launch pad or shopping assistant apparatus at entrance to a store or shopping areas. In the current example, a footwear application is described. The apparatus subsequently measures/scans the users body area, such as feet, and thereafter the apparatus, or cloud network, may process the user data and generate a user shopping avatar. Once generated the avatar is sent to the user's mobile device, running the shopping assistant Application, for example using mail, beacon, SMS, QR code, IR beam etc. The user may then scan wanted shoes, whereby the apparatus is configured to match and then try on shoes wanted to an avatar to provide best fit. The apparatus, in the current embodiment, may provide to the user expert or consulting information, thereby functioning at least in part as a sales representative. The apparatus may also provide related product information, such as availability, colors, sizes, related shoes, and rankings, as well as an Option to measure movement/style/weight etc.

In a third user case of the present invention, an augmented shopping experience may be delivered, whereby the automated shopping assistance process may incorporate a local shoe scan. In some cases user data or avatar's may be used to filter in appropriate reviews/comments from online world+social feedback+rankings, sales information/history, recommendations, up sales, cross sales etc.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:
1. A personalized shopping assistant system, comprising:
a Point of Sale based automated shopping assistant apparatus configured to generate a user shopping profile based on a capture of at least a part of a body of a user;
a shopping assistant server connected to a shopping assistant database and based in a communications cloud, wherein the shopping assistant server is configured to upload the user shopping profile to the shopping assistant database;
a mobile device application configured to the user shopping profile in a store using a mobile device of the user;
a plurality of product identifiers configured to enable the user to capture selected products using the mobile device application, wherein the plurality of product identifiers include scannable product data that is stored on the shopping assistant database;

a product selection module configured to interactively and selectably provide the user with automated product matching of one or more selected products in a store by using a matching algorithm to compare one or more parameters associated with the user shopping profile to one or more parameters of one or more products in the shopping assistance database to identify one or more matched products;

a digital avatar profile module configured to:
  generate a personalized user avatar profile based on the user shopping profile and the capture of at least a part of the body of the user;
  display one or more matched products on the personalized user avatar profile and a color heat map indicating one of a tightness, tension, or friction of the one or more matched products on the part of the body of the user;
  receive feedback in connection with the personalized user avatar profile and color heat map; and
  display one or more updated matched products on the personalized user avatar profile, wherein the one or more updated matched products are selected in accordance with the received feedback; and a point of sale assistance device located at the Point of Sale and configured to:
  prompt a sales associate at the Point of Sale to provide feedback in connection with the one or more matched products displayed on the personalized user avatar profile and the color heat map; and
  transmit, to the mobile device, the feedback from the sales associate at the Point of Sale in connection with the one or more matched products displayed on the personalized user avatar profile and the color heat map.

2. The personalized shopping assistant system of claim 1, wherein the Point of Sale based automated shopping assistant apparatus includes one or more image scanners configured to capture at least a part of a body that relates to an anatomical profile of the user, and to enable capture of length, breadth and depth of the part of the body.

3. The personalized shopping assistant system of claim 1, wherein the Point of Sale based automated shopping assistant apparatus includes one or more pressure sensors configured to capture a depth impression of at least a part of a body that relates to an anatomical profile of the user.

4. The personalized shopping assistant system of claim 1, wherein the Point of Sale based automated shopping assistant apparatus includes one or more light sources configured to capture a depth impression of at least a part of a body that relates to an anatomical profile of the user.

5. The personalized shopping assistant system of claim 1, further comprising a proximity sensor associated with the Point of Sale based automated shopping assistant apparatus configured to identify when a user enters a selected geographical zone around the Point of Sale based automated shopping assistant apparatus and to identify the user shopping profile associated with the user.

6. The personalized shopping assistant system of claim 1, further comprising a proximity sensor associated with the Point of Sale based automated shopping assistant apparatus configured to automatically trigger a scan when the user is positioned in a proximity of the proximity sensor.

7. The personalized shopping assistant system of claim 1, further comprising a shopping profile sharing module configured to enable the user to shop for a second user, when authorized, using a shopping profile of the second user.

8. The personalized shopping assistant system of claim 1, wherein the user shopping profile includes a feet profile configured to enable footwear matching.

9. The personalized shopping assistant system of claim 1, wherein the product selection module is further configured to receive user selections to determine user updates to be made to the user shopping profile.

10. The personalized shopping assistant system of claim 1, wherein the product selection module is further configured to receive, from the shopping assistant server, advanced product data to determine at least one of: purchasing options, inventory status, product qualities, product features, and reviews, and wherein the one or more matched products are identified based, at least in part, on the advanced product data.

11. The personalized shopping assistant system of claim 1, wherein the point of sale assistance device is further configured to provide advanced filtering of one or more additional product recommendations based on information related to the products available at the Point of Sale and based on the feedback from the sales associate at the Point of Sale in connection with the one or more matched products displayed on the personalized user avatar profile and the color heat map.

* * * * *